US010414722B2

(12) United States Patent
Goudreau et al.

(10) Patent No.: US 10,414,722 B2
(45) Date of Patent: Sep. 17, 2019

(54) BIOINSPIRED CATALYSIS USING OLIGOUREA HELICAL FOLDAMERS

(71) Applicants: Centre National De La Recherche Scientifique (CNRS), Paris (FR); UREKA SARL, Mulhouse (FR)

(72) Inventors: Sebastien Goudreau, Bordeaux (FR); Gilles Guichard, Gradignan (FR); Lucile Fischer, Camblannes et Maynac (FR); Arnaud Salaun, Sarzeau (FR); Vincent Diemer, Roubaix (FR); Diane Becart, Antony (FR)

(73) Assignees: UREKA SARL, Mulhouse (FR); CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 0 days.

(21) Appl. No.: 15/189,937

(22) Filed: Jun. 22, 2016

(65) Prior Publication Data
US 2016/0368864 A1    Dec. 22, 2016

Related U.S. Application Data

(60) Provisional application No. 62/182,997, filed on Jun. 22, 2015.

(51) Int. Cl.
| | | |
|---|---|---|
| *C07C 275/40* | (2006.01) | |
| *B01J 31/02* | (2006.01) | |
| *C07C 275/30* | (2006.01) | |
| *C07C 335/16* | (2006.01) | |
| *C07D 207/09* | (2006.01) | |

(52) U.S. Cl.
CPC ......... *C07C 275/40* (2013.01); *B01J 31/0235* (2013.01); *C07C 275/30* (2013.01); *C07C 335/16* (2013.01); *C07D 207/09* (2013.01)

(58) Field of Classification Search
CPC .... C07C 275/40; C07C 275/30; C07C 335/16
USPC ....................................... 514/453, 483, 616
See application file for complete search history.

(56) References Cited

U.S. PATENT DOCUMENTS

| | | | |
|---|---|---|---|
| 5,424,286 A | 6/1995 | Eng | |
| 5,595,756 A | 1/1997 | Bally et al. | |
| 6,958,384 B2 | 10/2005 | Gellman et al. | |
| 7,060,845 B2 | 6/2006 | Guichard | |
| 7,186,828 B2 | 3/2007 | Guichard | |
| 7,691,807 B2 | 4/2010 | Violette et al. | |
| 7,858,737 B2 | 12/2010 | Gellman et al. | |
| 8,138,145 B2 | 3/2012 | Violette et al. | |
| 9,243,040 B2 | 1/2016 | Cheng | |
| 2002/0143191 A1 | 10/2002 | Guichard | |
| 2005/0038105 A1* | 2/2005 | Guichard | C07C 275/24 514/453 |
| 2006/0211625 A1 | 9/2006 | Violette | |
| 2010/0099185 A1 | 4/2010 | Horne | |
| 2011/0118440 A1 | 5/2011 | Gellman et al. | |
| 2012/0021530 A1 | 6/2012 | Gellman et al. | |
| 2015/0141323 A1 | 5/2015 | Ureka | |

FOREIGN PATENT DOCUMENTS

| | | |
|---|---|---|
| EP | 1640361 A2 | 3/2006 |
| WO | WO 2003/029198 A1 | 4/2003 |
| WO | WO 2012/085479 | 6/2012 |
| WO | WO 2013/102209 | 7/2013 |
| WO | WO 2015/024955 A1 | 2/2015 |
| WO | WO 2017/037142 | 3/2017 |
| WO | WO 2017/037150 | 3/2017 |

OTHER PUBLICATIONS

Pendem (Angewandte Chemie International Edition; 2013, 4147-4151).*
Fischer; Angewandte Chemie International Edition; 2010, 49, 1067-1070.*
Fischer; Angewandte Chemie International Edition; 2010, 49, 1067-1070, supporting information.*
International Search Report, dated Oct. 12, 2016, for PCT/IB2016/001007.
Written Opinion for International Search Report, dated Oct. 12, 2016, for PCT/IB2016/001007.
Romina Wechsel et al: "Inducing achiral aliphatic oligoureas to fold into helical conformations", Chemical Communications—Chemcom., vol. 50, No. 95, Jan. 1, 2014 (Jan. 1, 2014), pp. 15006-15009, XP055306182, ISSN:1359-7345, DOI: 10.1039/C4CC06754A.
Aude Violette et al: "Mimicking Helical Antibacterial Peptides with Nonpeptidic Folding Oligomers", Chemistry and Biology., vol. 13, No. 5, May 1, 2006 (May 1, 2006), pp. 531-538, XP055307145, GB ISSN: 1074-5521, DOI: 10.1016/j.chembiol.2006.03.009.
Hemmerlin C et al: "Helix-forming oligoureas: Temperature-dependent NMR, structure determination, and circular dichroism of a nonamer with functionalized side chains", Helvetica Chimica Acta, Verlag Helvetica Chimica Acta, CH, vol. 85, No. 11, Jan. 1, 2002 (Jan. 1, 2002), pp. 3692-3711, XP002417783, ISSN: 0018-019X, DOI: 10.1002/1522-2675(200211)85:11<3692::AID-HLCA3692>3.0.00;2-W oligoureas 1 and 2.
Aude Violette et al: "N,N"-Linked Oligoureas as Foldamers: Chain Length Requirements for Helix Formation in Protic Solvent Investigated by Circular Dichroism, NMR Spectroscopy, and Molecular Dynamics", Journal of the American Chemical Society, vol. 127, No. 7, Feb. 1, 2005 (Feb. 1, 2005), pp. 2156-2164, XP055152097, ISSN: 0002-7863, DOI: 10.1021/ja044392b.

(Continued)

*Primary Examiner* — Pancham Bakshi
(74) *Attorney, Agent, or Firm* — Bryan D. Zerhusen, Esq.; Cantour Colburn LLP

(57) ABSTRACT

The present description provides oligourea catalysts, a polar helical oligomeric strands, and methods for catalyzing reactions with polar helical oligomeric strands and oligourea catalysts. In particular, the invention relates to a polar helical oligomeric strand of at least 4 residues selected from the formula (I) and which can be used as a catalyst.

21 Claims, 7 Drawing Sheets

(56) References Cited

OTHER PUBLICATIONS

Wiszniewska, Anna et al: "Synthesis of peptidomimetics: An evaluation of p-nitrophenyl carbamate of ethylenediamine", Letters in Peptide Science, Jan. 1, 2003 (Jan. 1, 2003), pp. 33-39, XP055307149, Dordrecht DOI: 10.1007/13F02443640 Retrieved from the Internet: URL:http://rd.springer.com/content/pdf/10.1023/B:LIPS.0000014027.84594.e6.pdf.
Curran, D. P.; Kuo, L. H. Altering the Stereochemistry of Allylation Reactions of Cyclic .alpha.-Sulfinyl Radicals with Diarylureas. J. Org. Chem. 1994, 59, 3259-3261.
Doyle, A. G.; Jacobsen, E. N. Small-molecule H-bond donors in asymmetric catalysis. Chem. Rev. 2007, 107, 5713-43.
Connon, S. J. Organocatalysis mediated by (thio)urea derivatives. Chem. Eur. J. 2006, 12, 5418-27; Takemoto, Y. Recognition and activation by ureas and thioureas: stereoselective reactions using ureas and thioureas as hydrogen-bonding donors. Org. Biomol. Chem. 2005, 3, 4299-306.
Jones, C. R.; Pantos, G. D.; Morrison, A. J.; Smith, M. D. Plagiarizing proteins: enhancing efficiency in asymmetric hydrogen-bonding catalysis through positive cooperativity. Angew. Chem. Int. Ed. Engl. 2009, 48, 7391-4.
Berkessel, A.; Roland, K.; Neudorfl, J. M. Asymmetric Morita-Baylis-Hillman Reaction Catalyzed by Isophoronediamine-Derived Bis(thio)urea Organocatalysts. Org. Lett. 2006, 8, 4195-4198.
Guichard, G.; Huc, I. Synthetic foldamers. Chem Commun (Camb) 2011, 47, 5933-41.
Fischer, L.; Guichard, G. Folding and self-assembly of aromatic and aliphatic urea oligomers: Towards connecting structure and function. Org. Biomol. Chem. 2010, 8, 3101-3117.
Pendem, N.; Nelli, Y. R.; Douat, C.; Fischer, L.; Laguerre, M.; Ennifar, E.; Kauffmann, B.; Guichard, G. Controlling Helix Formation in the γ-Peptide Superfamily: Heterogeneous Foldamers with Urea/Amide and Urea/Carbamate Backbones. Angew. Chem. Int. Ed. 2013, 52, 4147-4151.
Pendem, N.; Douat, C.; Claudon, P.; Laguerre, M.; Castano, S.; Desbat, B.; Cavagnat, D.; Ennifar, E.; Kauffmann, B.; Guichard, G. Helix-Forming Propensity of Aliphatic Urea Oligomers Incorporating Noncanonical Residue Substitution Patterns. J. Am. Chem. Soc. 2013, 135, 4884-4892.
Fischer, L.; Claudon, P.; Pendem, N.; Miclet, E.; Didierjean, C.; Ennifar, E.; Guichard, G. The Canonical Helix of Urea Oligomers at Atomic Resolution. Insight Into Folding-induced Axial Organization. Angew. Chem. Int. Ed. Engl. 2010, 49, 1067-1070.
Claudon, P.; Violette, A.; Lamour, K.; Decossas, M.; Fournel, S.; Heurtault, B.; Godet, J.; Mély, Y.; Jamart-Grégoire, B.; Averlant-Petit, M.-C.; Briand, J.-P.; Duportail, G.; Monteil, H.; Guichard, G. Consequences of Isostructural Main-Chain Modifications for the Design of Antimicrobial Foldamers: Helical Mimics of Host-Defense Peptides Based on a Heterogeneous Amide/Urea Backbone. Angew. Chem. Int. Ed. Engl. 2010, 49, 333-336.
Okino, T.; Hoashi, Y.; Takemoto, Y. Enantioselective Michael Reaction of Malonates to Nitroolefins Catalyzed by Bifunctional Organocatalysts. J. Am. Chem. Soc. 2003, 125, 12672-12673.
Connon, S. J. Organocatalysis mediated by (thio)urea derivatives. Chem. Eur. J. 2006, 12, 5418-27.
Jakab, G.; Tancon, C.; Zhang, Z.; Lippert, K. M.; Schreiner, P. R. (Thio)urea Organocatalyst Equilibrium Acidities in DMSO. Org. Lett. 2012, 14, 1724-1727.
Nelli, Y. R.; Antunes, S.; Salaün, A.; Thinon, E.; Massip, S.; Kauffmann, B.; Douat, C.; Guichard, G. Isosteric Substitutions of Urea to Thiourea and Selenourea in Aliphatic Oligourea Foldamers: Site-Specific Perturbation of the Helix Geometry. Chem. Eur. J. 2015, 21, 2870-2880.
Adams, P. D. et al. "PHENIX: a comprehensive Python-based system for macromolecular structure solution", Acta Crystallogr. D Biol. Crystallogr. 66, 213-221 (2010).

Aisenbrey, C., et al., "Solid state NMR studies of oligourea foldamers: interaction of 15N-labelled amphiphilic helices with oriented lipid membanes", Org. Biomol. Chem., 10, 1440-1447 (2012).
Arup Roy et al: "Diversifying the structural architecture of synthetic oligomers: the hetero foldamer approach", Chemical Communications, 47(42):11593-11611, Jan. 1, 2011.
Arvidsson, et al., On the Antimicrobial and Hemolytic Activities of Amphiphilic Beta-peptides. ChemBioChem, 2001, 10, 771-3.
Ballaster, P. Chem. Soc. Rev. 2010, 39 (10), 3810.
Bathany, K., et al., "Sequencing of oligourea foldamers by tandem mass spectrometry", Journal of the American Society for Mass Spectrometry, Feb. 12, 2013, 24(3):458-462.
Beck, et al., Angew. Chem. Int. Engl. 2015, 54 (3), 937.
Biros, S. M., et al. Chem. Soc. Rev. 2007, 36 (1), 93.
Boeijen, A., et a., J. Org. Chem, 2001, 66, 8454.
Boeijen, et al., "Solid-Phase Synthesis of Oligourea Peptidomimetics", Eur. J. Org. Chem., 1999, 2127-35.
Bouillere, F., et al., "Foldamers containing c-amino acid residues or their analogues: structural features and applications", Amino Acids, 41, 687-707 (2011).
Bromley, et al., "Peptide and protein building blocks for synthetic biology: from programming biomolecules to self-organized biomolecular systems", ACS Chem. Biol. 3, 38-50 (2008).
Brown, R.A., et al., Angew Chem Int Ed. 2012, 51, 1395-1399.
Burgess, et al., "Solid Phase Synthesis of Oligoureas", J. of American Chem. Soc. v119(7): 1556-1564 (1997).
Burgess, et al., "Solid-phase syntheses of unnatural biopolymers containing repeating urea units", Agnew. Chem. Int. Ed. Engl. 34, 907-909 (1995).
Castelletto, et al., Amyloid peptides incorporating a core sequence from the amyloid beta peptide and gamma amino acids: relating bioactivity to self-assembly, Chem. Commun., 2011, 47, 12470-12472.
Chandramouli, N., et al. Nat. Chem. 2015, 7 (4), 334.
Chen, et al., "Determination of the Secondary Structures of Proteins by Circular Dichroism and Optical Rotatory Dispersion", Biochem. vol. 11, No. 22, 1972, pp. 4120-4131.
Chicchi, et al., "Alterations in receptor activation and divalent cation activation of agonist binding by deletion of intracellular domains of the glucagon receptor", J. Biol. Chem., 272: pp. 7765 (1997).
Cho, C., et al., Science 1993, 261, 1303-1305.
Cho., C., et al., J. Am. Chem. Soc. 1998, 120(31), 7706-7718.
Choi, Soo Hyuk, "Helical structures of unnatural peptides for biological applications", Biomedical Engineering Letters, vol. 3., No. 4, pp. 226-231, Dec. 1, 2013.
Collie, Gavin W., et al., "Shaping quaternary assemblies of water-soluable non-peptide helical goldamers by sequence manipulation", Nature Chemistry, vol. 7, No. 11, Sep. 28, 2015, pp. 871-878.
Conn, M. M., et al. Chem. Rev. 1997, 97 (5), 1647.
Coward, "N—Me—pAB-Glu-gamma-Glu-gamma-Tyr(3-NO2): An Internally Quenched Fluorogenic Gamma-glutamyl Hudrolase Substrate", Bioorganic & Medicinal Chemistry Letters, Oxford GB, v11(12): 1561-1564 (2001).
Craig, et al. ChemBioChem 2011, 12 (7), 1035.
Daniels, D. S., "High-resolution structure of a beta-peptide bundle", J. Am. Chem. Soc. 129, 1532-1533 (2007).
Delano, W.L., "The PyMOL molecular graphic system", DeLano Scientific, San Carols, CA (2002).
Der, et al., "The use of coiled coils could facilitate the modular, predictable design of protein nanocages", Nat. Biotechnol, 31 (9) 809-810 (2013).
Douat, Celine, et al., "A Cell-penetrating foldamer with a bioreducible linkage for intracellular delivery of DNA, "Angewaandte Chemie, vol. 127, No. 38, pp. 11285-11289, Aug. 5, 2015.
Douat-Casassus, et al., "Microwave-enhanced solid-phase synthesis of N,N'-linked aliphatic oligoureas and related hybrids", Org. Lett. 14,3130-3133 (2012).
Ebalunode, et al., Bioorg. Med. Chem. 2009, 17 (14) 5133.
Emsley, et al., "Features and development of Coot", Acta Crystallogr. D Biol. Crystallogr. 66, 486-501 (2010).
Evans, P. "Scaling and assessment of data quality", Acta Crystallogr. D Biol. Crystallogr.,D 62 (Pt 1) 72-82 (2006).

(56) References Cited

OTHER PUBLICATIONS

Faiella, M. et al. "An artificial di-iron oxo-protein with phenol oxidase activity", Nat. Chem. Biol. 5(12), 882-884 (2009) (Published in final form as Nat Chem Biol . Dec. 2009 ; 5(12): doi:10.1038/nchembio.257.pp. 1-7).
Ferrand, Y., et al. "Diastereoselective Encapsulation of Tartaric Acid by a Helical Aromatic Oligoamide", J. Am. Chem. Soc., 132 (23), 7858-7859 (2010).
Fischer Lucile, "Succinimidyl carbamate derivatives from N-protected alpha-amino acids and dipeptides—Synthesis of Ureidopeptides and Oligourea/Peptide Hybrids", European Journal of Organic Chemistry, No. 15:2511-2525, May 1, 2007.
Fischer, L., et al., "The canonical helix of urea oligomers at atomic resolution: insights into folding-induced axial organization", Angew. Chem. Int. Ed. Engl. 2010, 122, 1085-1088.
Fletcher, et al., "Self-assembling cages from coiled-coil peptide modules", Science 340,595-599 (2013)—ScienceExpress http://www.sciencemag.org/content/early/recent / Apr. 11, 2013 / p. 1 / 10.1126/science. 1233936.
Frackenpohl, et al., "The outstanding biological stability of beta- and gama-peptides toward proteylytic enzymes: an in vitro investigation with fifteen peptidases", Chembiochem 2, 445-455 (2001).
Fremaux, J. et al. "α-Peptide/Oligourea Chimeras: Stabilization of Short α-helices by Non Peptide Helical Foldamers", Angew. Chem. Int. Ed. Engl. , vol. 127, No. 34., Aug. 17, 2015, pp. 9954-9958 DOI: 10.1002/anie.201500901R201500901.
Gao, Yi et al., "Theoretical Study of the Secondary Structures of Unionized Poly(y-D-glutamic acid)", Molecular Physics (2004), 102(23-24).
Garric, J., et al. "Encapsulation of Small Polar Guests in Molecular Apple Peels", Chemistry, 13 (30), 8454-8462 (2007).
Garric, J., et al. "Molecular Apple Peels", Angew. Chem. Int. Ed. Engl., 44 (13), 1954-1958 (2005).
Gellman, et al., "Foldamers: A Manifesto", Acc. Chem. Res. 31, 173-180 (1998).
Gennari, C., et al., Angew. Chem. Int. Ed. 1994, 33, 2067-2069.
Ghirlanda, G. et al. "Volatile anesthetic modulation of oligomerization equilibria in a hexameric model peptide", FEBS Lett. 578, 140-144 (2004).
Giuliano, M. W., et al. "An alpha/beta-peptide helix bundle with a pure beta3-amino acid core and a distinctive quaternary structure", J. Am. Chem. Soc. 131, 9860-9861 (2009).
Goodman, et al. J. Am. Chem. Soc. 2007, 129 (47), 14746.
Goodman, et al., "Foldamers as versatile frameworks for the design and evolution of function", Nat. Chem Biol. 3, 252-262 (207).
Gradišar, et al., "Design of a single-chain polypeptide tetrahedron assembled from coiled-coil segments", Nat. Chem. Biol. 9, 362-366 (2013).
Gradišar, et al., "Self-assembled bionanostructures: proteins following the lead of DNA nanostructures", J. Nanobiotechnology 12, 4, 1-9, (2014).
Guichard, G., et al., "Effective Preparation of O-succinimidyl-2(tert-butoxycarbonylamino)ethylcarbamate derivatives from B-amino Acids. Application to the synthesis of urea-containing pseudopeptides and oligoureas", J. Org. Chem. 1999, 64, 8702-8705.
Guichard, G., et al., Magn. Reson. Chem., 2008, 46, 918-924.
Gura, "Cancer Models: Systems for Identifying New Drugs are Often Faulty", Science vol. 278 (1997), 10411042 provided as HTML file pp. 1-5.
Hamuro et al., "De Novo Design of Antibacterial B-Peptides", J. Am. Chem. Soc., 1999, 121, 12200-12201.
Harbury, P. B., et al., "High-resolution protein design with backbone freedom", Science 282, 1462-1467 (1998).
Hernandez, H., et al., "Determining the stoichiometry and interactions of macromolecular assemblies from mass spectrometry", Nat. Protoc. 2, 715-726 (2007).
Hill, R. et al, "De novo design of helical bundles as models for understanding protein folding and function", Acc. Chem. Res. 33, 745-754 (2000).

Hintermann, et al., "Gamma-Peptides Forming More Stable Secondary Structures Than Alpha-Peptides: Synthetis and Helical NMR-Solution Structure of The Hexapeptide Analong of H-(Val-Ala-Leu)2-0H", Helvetica Chimica Acta., v81: 983-1002 (1998).
Horne, et al. "Interplay among side chain sequence, backbone composition, and residue rigidification in polypeptide folding and assembly", Proc. Natl. Acad. Sci. U.S.S., 105 (27) 9151-9156 (2008).
Horne, et al., "Helix bundle quaternary structure from alpha/beta-peptide foldamers", J. Am. Chem. Soc. 129, 4178-4180 (2007).
Horne, W.S., et al., "Foldamers with Heterogeneous Backbones", Acc. Chem. Res., 41, 1399-1408 (2008).
Hua, Y., et al. "Hydrophobic Collapse of Foldamer Capsules Drives Picomolar-Level Chloride Binding in Aqueous Acetonitrile Solutions", J. Am. Chem. Soc., 135 (38), 14401-14412 (2013).
Inouye, M., et al. "Saccharide-Dependent Induction of Chiral Helicity in Achiral Synthetic Hydrogen-Bonding Oligomers", J. Am. Chem. Soc., 126 (7), 2022-2027 (2004).
Joh, N. H. et al., "De novo design of a transmembrane Zn2+—transporting four-helix bundle", Science 346, 1520-1524 (2014).
Johansson, et al., "A Designed Cavity in the Hydrophobic Core of a Four-α-Helix Bundle Improves Volatile Anesthetic Binding Affinity", Biochemistry 1998, 37 (5) 1421-1429.
Johnson, et al., "a-Helix mimicry with a/β-peptides", Methods Enzymol 523, 407-429 (2013).
Juwarker, H., et al. Chem. Soc. Rev. 2009, 38 (12), 3316.
Kabsch, W. "XDS", Acta Crystallogr. D Biol. Crystallogr. 66, 125-132 (2010)) and CCP4 (Winn, M. D. et al. Overview of the CCP4 suite and current developments. Acta Crystallogr. D Biol. Crystallogr. 67, 235-242 (2011).
Kichler, A., et al., "Histidine-rich amphipathic peptide antibiotics promote efficient delivery of DNA into mammalian cells", Proc. Natl. Acad. Sci. USA,100, 1564-1568 (2003).
Kim, J., et al., Tetrahedron Letter., 1996, 37, 5305.
King et al., "Computational design of self-assembling protein nanomaterials with atomic level accuracy", Science 336, 1171-1174 (2012).
King, et al., "Accurate design of co-assembling multi-component protein nanomaterials", Nature 510, 103-108 (2014).
Kodakek.T., et al., "The Rise, Fall and Reinvention of Combinatorial Chemistry", Chem. Commun., 47, 9757-9763 (2011).
Kofoed, J., et al., "A General Method for Designing Combinatorial Peptide Libraries Decodable by Amino Acid Analysis", J. Comb. Chem., 9, 1046-1052 (2007).
Koziara, K. B., et al. J. Comput. Aided Mol. Des. 2014, 28 (3), 221.
Lai, et al., "Principles for designing ordered protein assemblies"., Tends Cell Biol. 22, 653-661 (2012).
Lai, et al., "Structure of a 16-nm cage designed by using protein oligomers", Science 336, 1129 (2012).
Lai, et al., "Structure of a designed protein cage that self-assembles into a highly porous cube", Nat. Chem 6, 1065-1071 (2014).
Laskowski, R.A. "SURFNET: a program for visualizing molecular surfaces, cavities and intermolecular interactions", J. Mol. Graph. 13, 323-330 (1995).
Lear, J. D., et al., "Synthetic amphiphilic peptide models for protein ion channels", Science 240, 1177-1181 (1988).
Legrand, B., et al., Angew. Chem. Int. Ed., 2012, 51, 11267-11270.
LePlae et al. "Tolerance of Acyclic Residues in the Beta-Peptide 12-Helix: Access to Diverse Side-Chain Arrays for Biological Applications". J. Am. Chem. Soc., 2002, 124, 6820-1.
Li, X., et al., Chem. Commun. 2006, 3367-3379.
Liu et al., "De Novo Design, Synthesis, and Characterization of Antimicrobial B-Peptides", J. Am Chem. Soc., 123, 7553-9 (2001).
Liu, et al., "Atomic structure of a tryptophan-zipper pentamer", Proc. Natl. Sci. U.S.A. 2004, 101 (46) 16156-16161 (2004).
Liu, R., Loll, P. J. & Eckenhoff, R. G. "Structural basis for high-affinity volatile anesthetic binding in a natural 4-helix bundle protein", FASEB J. 19, 567-576 (2005).
Lombardo, C.M., et al., "Anatomy of an oligourea six-helix bundle", Journal of the American Chemical Society, Aug. 24, 2016, vol. 138, No. 33, pp. 10522-10530.

(56) References Cited

OTHER PUBLICATIONS

Maity, B., et al. Curr. Opin. Chem. Biol. 2015, 25, 88.
McCoy, A. J. et al. "Phaser crystallographic software", J. Appl. Crystallogr. 40, 658-674 (2007).
Mecozzi, S., et al. Chem. Eur. J. 1998, 4 (6), 1016.
Murshudov, G. N. et al., "REFMAC5 for the refinement of macromolecular crystal structures", Acta Crystallogr. D Biol. Crystallogr. 67, 355-367 (2011).
Nelli, et al., "Structural characterization of short hybrid urea/carbamate (U/C) foldamers: a case of partial helix unwinding", Biopolymers 100, 687-697 (2013).
Nelli, Y.R., et al, "Structural characterization of short hybrid urea/carbamate (U/C) foldamers: A case of partial helix unwinding", Biopolymers. Nov. 2013;100(6):687-97. doi: 10.1002/bip.22302.
Nelli, Y.R., et al., Tetrahedron, 2012, 68, 4492.
O'Shea, E.K., et al., "X-ray structure of the GCN4 leucine zipper, a two-stranded, parallel coiled coil", Science 254, 539-544 (1991).
Oh, et al., "Design, synthesis and characterization of antimicrobial pseudopeptides corresponding to membrane-active peptide", J. Peptide Res., 1999, 54, 129-136.
Oostenbrink, C., et al. J. Comput. Chem. 2004, 25 (13), 1656.
Patch, et al., "Mimicry of bioactive peptides via non-natural, sequence-specific peptidomimetic oligomers", Curr. Op. Chem. Bio., 2002, 6, 872-877.
Pendem, N., et al., Angew, Chem. Int. Ed., 2013, DOI: 10.1002/anie.201209838.
Pizzey, et al., "Characterization of nanofibers formed by self-assembly of beta-peptide oligomers using small angle x-ray scattering", J. Chem. Phys. 129, 095103 (2008).
Pomerantz, W. C. et al., "Nanofibers and lyotropic liquid crystals from a class of self-assembling beta-peptides", Angew. Chem. Int Ed Engl. 47, 1241-1244 (2008).
Porter et al., "Mimicry of Host-Defense Peptides by Unnatural Oligomers: Antimicrobial Beta-Peptides", J. Am. Chem. Soc., 2002, 124, 7324-30.
Porter et al., "Non-Haemolytic Beta-Amino-Acid Oligomers", Nature, 2000, 404, 565.
Pronk, S., et al., "Gromacs 4.5: a high-throughput and highly parallel open source molecular simulation toolkit", Bioinformatics, 29 (7), 845-854 (2013).
Rebilly, J.-N., et al. Chem. Soc. Rev., 44 (2), 467 (2015).
Reig, et al., "Altering the $O_2$-Dependent Reactivity of de novo due ferri proteins", Nat, Chem., 4 (11), 900-906 (2012).
Remington: The Science and Practice of Pharmacy, 20th Edition, A. R. Gennaro, Ed., Lippincott Williams & Wilkins, (2000), pp. 721-727.
Remington's Pharmaceutical Sciences, 1980, vol. 16, Mack Publishing Company, Easton, Pa., pp. 61 and 424.
Rufo, et al., "Short peptides self-assemble to produce catalytic amyloids", Nat. Chem. 6 (4), 303-309 (2014).
Runge, et al., "Different domains of the glucagon and glucagon-like peptide-1 receptors provide the critical determinants of ligand selectivity", Brit. J. Pharmacol., 138: pp. 787-794 (2003).
Schuttelkopf, et al., "PRODRG: a tool for high-throughput crystallography of protein-ligand complexes", Acta Crystallogr. D Biol. Crystallogr. 60, 1355-1363 (2004).
Seebach, D., et al., "The World of b- and g-Peptides Comprised of Homologated Proteinogenic Amino Acids and Other Components", Chem. Biodivers. 2004, 1, 1111-1239.
Semetey, V., et al., "Stable helical secondary structure in short-chain N,N-Linked oligoureas bearing proteininogenic side chains", Angew. Chem. Int. Ed., 41, 1893-1895 (2002).
Singleton, M. L., et al. Angew. Chem. Int. Ed. Engl. 2014, 53 (48), 13140.
Smith, L.J., et al., "Analysis of main chain torsion angles in proteins: prediction of NMR coupling constants for native and random coil conformations", J. Mol. Biol., 255, 494-506 (1996).
Smrcina, et al., Tetrahedron, 1997, 53, 12867-12874.
Sola, J., et al., Angew. Chem. Int. Ed. 2010, 49, 6836-6839.

Soth and Nowick, "A peptide/Oligourea/Azapeptide Hybrid That Adopts a Hairpin Turn", J. Org. Chem. 1999, 64, 276-281.
Sporn et. al., "Chemoprevention of Cancer," Carcinogenesis, vol. 21 (2000), 525-530.
Suk, J.-M., et al., "Indolocarbazole-Based Foldamers Capable of Binding Halides in Water", J. Am. Chem. Soc. 2008, 130 (36), 11868-11869.
Takemoto, Y. "Recognition and activation by ureas and thioureas: stereoselective reactions using ureas and thioureas as hydrogen-bonding donors", Org. Biomol. Chem. 2005, 3, 4299-306.
Tamilarasu, et al., "Targeting RNA with peptidomimetic oligomers in human cells", Biorg. Med. Chem. Let., 2001, 11, 505-7.
Tamilarasu, "High Affinity and Specific Binding of HIV-1 TAR RNA by a Tat-Derived Oligourea", Journal of the American Chemical Society (1999), 121(7), 1597-1598.
Tamilarasu, "Supporting Information—High Affinity and Specific Binding of HIV-1 TAR RNA by a Tat-Derived Oligourea", Journal of the American Chemical Society (1999), 121(7), pp. S1-S12.
Tanatani, A., et al. Angew. Chem. Int. Ed. Engl. 2002, 41 (2), 325.
Tebo, et al., "Artificial metalloenzymes derived from three-helix bundles", Curr. Opin. Chem. Biol. 25C, 65-70 (2015).
Tegoni, M., et al., "Designing a functional type 2 copper center that has nitrite reductase activity within α-helical coiled coils", Proc. Natl. Acad. Sci. U. S. A. 109, 21234-21239 (2012).
Toniolo, C., et al., Trends Biochem Sci. 1991, 16, 350-353.
Vallavoju, N.; Sivaguru, J. Chem. Soc. Rev. 2014, 43 (12), 4084.
Violette, A., et al., Chem. Eur. J. 2008, 14, 3874-3882.
Wang, P. S. P., et al., "Design and high-resolution structure of a β3-peptide bundle catalyst", J. Am. Chem. Soc. 136, 6810-6813 (2014).
Winn, M. D. et al., "Overview of the CCP4 suite and current developments", Acta Crystallogr. D Biol. Crystallogr. 67, 235-242 (2011).
Wiszniewska, et al., "p-Nitrophenoxycarbonyl derivatives of Boc-protected diaminoalkanes in the synthesis of encephalin peptidomimetics", J. Peptide Sci. 11:579-583 (2005).
Woolfson, D. N. "The design of coiled-coil structures and assemblies", Adv. Protein Chem. 70, 79-112 (2005).
Wu, et al., "Chloride Coordination by Oligoureas: From Mononuclear Crescents to Dinuclear Foldamers", Org. Lett. 2012, 14 (3), 684-687.
Xu, Y.-X., et al. "Folding of Aromatic Amide-Based Oligomers Induced by Benzene-1,3,5-tricarboxylate Anion in DMSO", J. Org. Chem. 2009, 74 (19), 7267-7273.
Yadav, et al. "Structure-based engineering of internal cavities in coiled-coil peptides", Biochemistry 44, 9723-9732 (2005).
Zaccai, et al., "A de novo peptide hexamer with a mutable channel", Nat. Chem. Biol. 7, 935-941 (2011).
Zarra, et al. Chem. Soc. Rev. 2015, 44 (2), 419.
Zhang, et al., "Structural DNA nanotechnology: state of the art and future perspective", J. Am. Chem. Soc. 136, 11198-11211 (2014).
Zhang, Z. & Fan, E. "Solid-phase and solution-phase syntheses of oligomeric guanidines bearing peptide side chains", J. Org. Chem. 80, 8801-8810 (2005).
Ballaster, P., "Anion binding in covalent and self-assembled molecular capsule", Chem. Soc. Rev. 2010, 39 (10), 3810-3830.
Beck, et al., "Construction of matryoshka-type structures from supercharged protein nanocages", Angew. Chem. Int. Engl. 2015, 54 (3), 937-940.
Biros, S. M., et al. "Structure and binding properties of water-soluble cavitands and capsules", Chem. Soc. Rev. 2007, 36 (1), 93-104.
Boeijen, A., et a., "Solid-Phase Synthesis of oligourea peptidomimetics employing the Fmoc protection strategy", J. Org. Chem, 2001, 66, 8454-8462.
Brown, R.A., et al., "Induction of unexpected left-handed helicity by an N-Terninal L-Amino acid in an otherwise aciral peptide chain", Angew Chem Int Ed. 2012, 51, 1395-1399.
Chandramouli, N., et al., Iterative design of a helically folded aromatic oligoamide sequence for the selective encapsulation of fructose, Nat. Chem. 2015, 7 (4), 334-341.
Cho, C., et al., "An unnatural Biopolymer", Science 1993, 261, 1303-1305.

(56) References Cited

OTHER PUBLICATIONS

Cho., C., et al., Synthesis and screening of linear and cyclic oligocarbamate libraries. Discovery of high affinity ligands for CPIIb/IIIa, J. Am. Chem. Soc. 1998, 120(31), 7706-7718.
Conn, M. M., et al., Self-assembling capsules, Chem. Rev. 1997, 97 (5), 1647-1668.
Craig, et al., "Enhancing β3-peptide bundle stability by design", ChemBioChem 2011, 12 (7), 1035-1038.
Douat, Celine, et al., "A Cell-penetrating foldamer with a bioreducible linkage for intracellular delivery of DNA, "Agnew Chem Int Ed, 2015, 55, 11133-11137.
Ebalunode, et al., "Structure-based shape pharmacophore modeling for the discovery of novel anesthetic compounds", Bioorg. Med. Chem. 2009, 17 (14) 5133-5138.
Fremaux, J., et al., "Influence of archiral unites with gem-dimethy substituents on the helical charater of aliphatic oligourea foldamers", Chem Comm (Camb). Aug. 28, 2013, 49(67); 7415-7. Doi:10.1039/c3cc40961a.
Fremaux, J., et al., G. "Condensation approach to aliphatic oligourea foldamers: helices with N-(pyrrolidin-2-ylmethyl)ureido junctions", Angew. Chem. Int. Ed Engl. 50, 11382-11385 (2011).
Fremaux, J. et al. "α-Peptide/Oligourea Chimeras: Stabilization of Short α-helices by Non Peptide Helical Foldamers", Angew. Chem. Int. Ed. Engl. , vol. 54, 2015, pp. 9816-9820 DOI: 10.1002/anie.201500901R201500901.
Gao, Yi et al., "Theoretical Study of the Secondary Structures of Unionized Poly(y-D-glutamic acid)", Molecular Physics (2004), 102(23-24) 2491-2498.
Garric, J., et al. "Encapsulation of Small Polar Guests in Molecular Apple Peels", Chemical Eng. Journal, 13 (30), 8454-8462 (2007).
Gennari, C., et al., "Synthesis of sulfonamide-pseudopeptides: new chiral unnatural oligomers", Angew. Chem. Int. Ed. 1994, 33, 2067-2069.
Goodman, et al., "Biophysical and structural characterization of a robust octameric β-peptide bundle", J. Am. Chem. Soc. 2007, 129 (47), 14746-14751.
Goodman, et al., "Foldamers as versatile frameworks for the design and evolution of function", Nat. Chem Biol. 3, 252-262 (2007).
Guichard, G., et al., "Solution structure determination of oligoureas using methylene spin state selective NMR at $^{13}C$ natural abundance", Magn. Reson. Chem., 2008, 46, 918-924.
Gura, "Cancer Models: Systems for Identifying New Drugs are Often Faulty", Science vol. 278 (1997), 1041-1042.
Hintermann, et al., "Gamma-Peptides Forming More Stable Secondary Structures Than Alpha-Peptides: Synthesis and Helical NMR-Solution Structure of the Hexapeptide Analong of H-(Val-Ala-Leu)2-0H", Helvetica Chimica Acta., v81: 983-1002 (1998).
Horne, et al. "Interplay among side chain sequence, backbone composition, and residue rigidification in polypeptide folding and assembly", Proc. Natl. Acad. Sci. U.S., 105 (27) 9151-9156 (2008).
Juwarker, H., et al., "Foldamers with helical cavities for binding complementary guests", Chem. Soc. Rev. 2009, 38 (12), 3316-3325.
Kim, J., et al., "The solid phase synthesis of oligoureas", Tetrahedron Letter., 1996, 37, 5305-5308.
King, et al., "Accurate design of co-assembling multi-component protein nanomaterials", Nature 510, 103-108 (2012).
Koziara, K. B., et al., "Testing and validation of the automated topology builder (ATB) version 2.0: prediction of hydration free enthalpies", J. Comput. Aided Mol. Des. 2014, 28 (3), 221-223.

Legrand, B., et al., "Robust helix formation in a new family of oligoureas based on a constrained bicyclic building block", Angew. Chem. Int. Ed., 2012, 51, 11267-11270.
Li, X., et al., "Peptides of aminoxy acids as foldamers", Chem. Commun. 2006, 3367-3379.
Liu et al., "De Novo Design, Synthesis, and Characterization of Antimicrobial B-Peptides", J. Am Chem. Soc., 123, 7553-7559 (2001).
Maity, B., et al. "Use of the confined spaces of apo-ferritin and virus capsids as nanoreactors for catalytic reactions", Curr. Opin. Chem. Biol. 2015, 25, 88-97.
Mecozzi, S., et al., "The 55% solution: a formula for molecular recognition in the Liquid State", Chem. Eur. J. 1998, 4 (6), 1016-1022.
Nelli, Y.R., et al., "An activated building block for the introduction of the histidine side chain in aliphatic oligourea foldamers", Tetrahedron, 2012, 68, 4492-4500.
Oostenbrink, C., et al., "A biomolecular force field based on the free enthalpy of hydration and solvation: the GROMOS force-field parameter sets 53A5 and 53A6", J. Comput. Chem. 2004, 25 (13), 1656-1676.
Rebilly, J.-N., et al., "Biomimetic cavity-based metal complexes", Chem. Soc. Rev., 44 (2), 467-489 (2015).
Singleton, M. L., et al., "Increasing the size of an aromatic helical foldamer cavity by strand intercalation", Angew. Chem. Int. Ed. Engl. 2014, 53 (48), 13140-13144.
Smrcina, et al., "Facile stereoselective synthesis of y-substituted y-amino acids from corresponding a-amino acids", Tetrahedron, 1997, 53, 12867-12874.
Sola, J., et al., "Nanometer-range communication of stereochemical information by reversible switching of molecular helicity", Angew. Chem. Int. Ed. 2010, 49, 6836-6839.
Takemoto, Y. "Recognition and activation by ureas and thioureas: stereoselective reactions using ureas and thioureas as hydrogen-bonding donors", Org. Biomol. Chem. 2005, 3, 4299-4306.
Tamilarasu, et al., "Targeting RNA with peptidomimetic oligomers in human cells", Biorg. Med. Chem. Let., 2001, 11, 505-507.
Tanatani, A., et al. "Foldamers as dynamic receptors: probing the mechanism of molecular association between helical oligomers and rodlike ligands", Angew. Chem. Int. Ed. Engl. 2002, 41 (2), 325.
Tebo, et al., "Artificial metalloenzymes derived from three-helix bundles", Curr. Opin. Chem. Biol. 25, 65-70 (2015).
Toniolo, C., et al., "The polypeptide 310-helix", Trends Biochem Sci. 1991, 16, 350-353.
Vallavoju, N. et al., "Supramolecular photocatalysis: combining confinement and non-covalent interactions to control light initiated reactions", J. Chem. Soc. Rev. 2014, 43 (12), 4084-4101.
Violette, A., et al., "Exploring helical folding of oligoureas during chain elongation by high-resolution magic-angle-spinning (HRMAS) NMR spectroscopy", Chem. Eur. J. 2008, 14, 3874-3882.
Wechsel, Romina, et al., "Inducing archiral aliphatic oligoureas to fold into helical conformations", Chemical Communications, vol. 50, No. 95, Jan. 1, 2014, pp. 15006-15009.
Zarra, et al., "Molecular containers in complex chemical systems", Chem. Soc. Rev. 2015, 44 (2), 419432.
International Search Report and Written Opinion for PCT/162017/000528, dated Jan. 19, 2018.

* cited by examiner

Takemoto's catalyst

BIOINSPIRED CATALYSIS USING OLIGOUREA HELICAL FOLDAMERS

CROSS-REFERENCE TO RELATED APPLICATIONS

This application claims priority to the U.S. Provisional Application No. 62/182,997, filed Jun. 22, 2015, which is incorporated herein by reference in its entirety.

FIELD OF THE INVENTION

The present description relates to oligourea compounds and their use as catalysts.

BACKGROUND

Interactions between proteins and/or their substrates or ligands are critical for normal cell function, physiologic signal transduction, as well as for therapeutic intervention in many pathophysiologic or disease-related processes. Proteins and peptides are capable of adopting compact, well-ordered conformations, and performing complex chemical operations, e.g., catalysis, highly selective recognition, etc. The three dimensional structure is the principal determinant that governs specificity in protein-protein and/or protein-substrate interactions. Thus, the conformation of peptides and proteins is central for their biological function, pharmaceutical efficacy, and their therapeutic preparation.

Protein folding is inextricably linked to function in both proteins and peptides because the creation of an "active site" requires proper positioning of reactive groups. Consequently, there has been a long-felt need to identify synthetic polymer or oligomers, which display discrete and predictable (i.e., stable) folding and oligomerizing propensities (hereinafter referred to as "foldamers") to mimic natural biological systems. Insofar as these unnatural backbones are resistant to the action of proteases and peptidases, they are useful as probes having constrained conformational flexibility or as therapeutics with improved pharmacological properties, e.g., pharmacokinetic (PK) and/or pharmacodynamics (PD) features, such as potency and/or half-life. Whereas a naturally occurring polypeptide comprised entirely of α-amino acid residues will be readily degraded by any number of proteases and peptidases, foldamers, including chimeras of natural peptides and synthetic amino acid derivatives, mimetics or pseudopeptides, are not.

As noted above, the interest in foldamers stems in part from their resistance to enzymatic degradation. They are also interesting molecules because of their conformational behavior. The elucidation of foldamers having discrete conformational propensities akin to those of natural proteins has led to explorations of peptides constructed from β-, γ-, or δ-amino acids. γ-Peptides containing residues bearing γ-substitution or α, γ-disubstitution or α, β, γ-trisubstitution have been shown to adopt a helical conformation defined by a 14-member turn that is stabilized by $C=O_{(i)} \rightarrow NH_{(i+3)}$ hydrogen bonds (see FIG. 1c). Both the $3_{14}$ and $2.5_{12}$ helical backbones have been found suitable for the design of stabilized helical peptides useful for therapeutic purposes. For example, in order to cluster polar residues on one face of the helix, amphiphilic $3_{14}$-helical β-peptides have been constructed from hydrophobic-cationic-hydrophobic- or hydrophobic-hydrophobic-cationic residue triads.

The ability to use double H-bonding with disubstituted (thio)ureas as an activation mechanism in catalysis is known. Additionally, disubsituted ureas with electron-withdrawing groups are known to readily form co-crystals with a variety of proton acceptors including carbonyl groups. It has also been shown that highly enantioselective reactions can be promoted by chiral (thio)urea derivatives. The general utility of monofunctional and bifunctional ureas and thioureas as acid catalysts has been intensively explored for the synthesis of enantiomerically enriched molecules.

A number of organocatalysts and processes, including cascade and multicomponent reactions, have been reported to date. Organocatalysts present a number of advantages: they are non-toxic, affordable, easy to handle, and they allow the use of metal-free procedures. However, one of the main drawbacks is the general need for high catalyst loads often comprised between 5-20 mol % which is of course detrimental for applications. Therefore, there is a need to develop more active organic catalysts, able to promote asymmetric chemical transformations in very low loadings. Some have proposed integrating positive cooperativity through folding to enhance catalyst efficiency. That is, preorganizing the catalyst through H-bonding could contribute to cooperative ligand binding, to greater stabilization of charged intermediates, and to minimize the entropic cost of transition state (TS) binding. By using an original turn mimetic structure that populates a well-defined hairpin conformation, conformationally defined, but still flexible thiourea catalysts for asymmetric synthesis can be generated. Currently known bis-thiourea catalysts do not involve intramolecular cooperative H-bonding.

Advance in the design of bioinspired folded systems raises new prospects for protein/nucleic acid mimicry and for the design of architectures with functions beyond that of natural biopolymers. A significant number of building blocks and related oligomers with high propensity for folding into structurally well-defined and ordered 3D architectures have been reported, and which have been termed Foldamers. The ability to precisely control monomer sequences (and appended side chains) in these non-natural systems opens up interesting opportunities for mimicking biopolymer structures and creating systems with new functions, including catalysts.

H-bonds provide a very versatile way to create intrastrand (either local or remote) connections useful to control folding in new oligomeric materials. Non-natural oligoamides represent the quintessential foldamers. The urea group which shares a number of features with the amide linkage, i.e. rigidity, planarity, polarity, and hydrogen bonding capacity is also an interesting linkage for the construction of folded architectures. For example, aliphatic N,N'-linked oligoureas have been developed as helical foldamers.

NMR spectroscopy and X-ray diffraction has been extensively used to characterize the helical conformation of oligoureas. For example, FIGS. 1 shows crystal structures of enantiopure N,N'-linked oligoureas ranging from 5 to 9 urea groups and containing exclusively acyclic residues with proteinogenic side chains. FIG. 1a shows a stereoview of a nona-urea. FIG. 1b shows a view along the helical axis. FIG. 1c shows the detail of the three-centered H-bonding. The similarity between the structures deduced earlier from NMR studies in solution is striking and underlines the excellent complementarities of the two techniques to analyze urea-based foldamers. This also demonstrates the robustness of the folding process, four acyclic residues being sufficient to drive complete helix formation.

Monomeric units with different substitution patterns and various degrees of preorganization may be employed to fine-tune the arrangement of functional groups at the helix surface, modulating the helix stability, and ultimately enabling the design of more effective peptide mimics and/or sophisticated folded architectures.

Foldamer synthesis is not limited to homogenous backbones and approaches based on sequences combining two or more types of monomers, i.e. heterogeneous foldamers. For example, isosteric monomers with proteinogenic side chains of general formula NH—CH(R)—CH2-X—CO, X=CH$_2$, NH, O can be combined to create new heterogeneous helical foldamers within the γ-peptide superfamily. These units are endowed with different folding propensities (U (X=NH)>A (X=CH$_2$)>C(X=O)), the stability of the resulting fold is controlled by the ratio of A, U and C units and by their sequence distribution. Oligomers consisting of 1:1 alternation of U and C (or A) linkages and 2:2 alternations of U and A units retain the ability to fold into well-defined helical structures. Structures at atomic resolution obtained provide guidelines for the design and development of a large ensemble of structurally-related, but chemically distinct helical backbones.

SUMMARY

The present description relates to the surprising and unexpected discovery that foldamers comprising urea-based peptidomimetic residues (oligoureas) may be utilized as catalysts. In particular, the description provides an oligourea catalyst comprising a polar helical oligomeric strand of at least 4 residues selected from the formula (I):

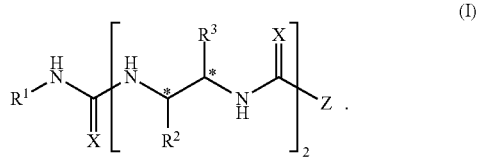

wherein X and Y are selected independently from O and S;

R$^1$ is independently selected from the group consisting of optionally substituted alkyl, optionally substituted aryl, optionally substituted heteroaryl, optionally substituted aralkyl, and optionally substituted heteroaralkyl;

R$^2$ and R$^3$ are independently selected from the group consisting of hydrogen; any side chain of a natural amino acid; Fluorine; linear, branched or cyclic C1-C6-alkyl, alkenyl or alkynyl; mono- or bicyclic aryl; mono or bicyclic heteroaryl having up to five heteroatoms selected from N, O and S; mono or bicyclic aryl-C1-C6-alkyl, alkenyl or alkynyl; trifluoromethyl; C1-C6-hydroxyle; C1-C6-alkyloxy, aryloxy, heteroaryloxy; C1-C6-alkylthio; C1-C6-amino; C1-C6-arylamino; arylamino; mono or di-C1-C6-alkylamino; mono or di-C1-C6-carboxylic acid; mono or di-C1-C6-alkylester; mono- or di-C1-C6-carboxamide; mono- or di-C1-C6-alkylcarboxamide; C1-C6-alkylsulfonamide; C1-C6-arylsulfonamide; C1-C6-sulfonamide; C1-C6-sulfamide; C1-C6-arylsulfamide C1-C6-urea; C1-C6-alkylurea; C1-C6-thiourea; C1-C6-alkylthiourea; C1-C6-guanidine; and C1-C6-alkylguanidine, benzamidine, C1-C6-benzamidine;

Z is a short oligomer of at least two residues selected from the group consisting of C-substituted and unsubstituted N-2-aminoethylcarbamoyl residue, C-substituted and unsubstituted N-(2-aminoethyl)carbamothioyl residues, C-substituted and unsubstituted γ-amino acid residue, —C-substituted and unsubstituted α-amino acids and any combination thereof. In a specific embodiment, the selected compound consists of a total number of 4-15 residues.

In certain aspects, the Z group is covalently linked to a solid-support. In certain aspects, the solid-support is selected from the group consisting of polystyrene, silica, and polyethylene glycol resins.

In any aspect or embodiment described herein, the foldamer compounds can further comprise at least one additional chemical modification. In certain embodiments, the chemical modification includes at least one of, for example, acetylation, phosphorylation, methylation, glycosylation, prenylation, isoprenylation, farnesylation, geranylation, pegylation, a disulfide bond, or combination thereof.

In an additional aspect, the description provides pharmaceutically acceptable acid and base salt forms of the foldamer compounds described herein.

The foldamers as described herein including pharmaceutically acceptable salts thereof are useful for the preparation of a medicament and/or the treatment of disease in a subject. The compounds of the invention may optionally be administered with at least one of a pharmaceutically acceptable excipient, pharmacologically active agent or a combination thereof. As such, in an addition aspect the description provides compositions comprising an effective amount of a compound as described herein, and a pharmaceutically acceptable carrier or excipient.

The description also provides methods of treating a disease or disorder or ameliorating the effects of the same comprising the steps of administering to an individual in need thereof, a composition comprising an effective amount of a compound or salt or prodrug form thereof as described herein, and a pharmaceutically acceptable carrier or excipient, wherein the composition is effective for treating, preventing or ameliorating the effects of the disease or disorder.

In one aspect, the description provides oligomeric compounds synthesized using the methods as described herein. The description also provides pharmaceutical compositions comprising effective amounts of said compounds. In other aspects, the description provides therapeutic methods comprising the administration of an effective amount of the compounds of the invention to a mammal in need thereof.

In another aspect, the present description provides methods of using the compounds as described herein. For example, the compounds as described herein can be used as a diagnostic agent or a therapeutic agent for the treatment of a disease or condition.

In an additional aspect the present description provides methods of making compounds as described herein. Thus, in one embodiment, the present description provides for the synthesis of non-natural amino acid foldamers substituted by a wide range of functional R groups including proteinogenic side chains. In another aspect, the description provides foldamers, which comprise non-natural oligourea amino acids (i.e., an amino acid having an N,N'-linked urea bridging unit) and or peptoid versions of the same together with natural amino acids, wherein the modified peptides or foldamers form functional biopolymers.

In any aspect or embodiment described herein, the description provides a method to catalyze reactions by acid catalysis (urea) with compounds described herein.

In any aspect or embodiment described herein, the description provides a method for catalysing the addition of nucleophiles C, H, O, P, S, Si, B, F, Cl, Br, I, or Sn.

In any aspect or embodiment described herein, the description provides a method of producing 1,2-additions on at least one of a carbonyl, C=N bond, C=S bond, C=C bond, C≡C, or C≡N.

In any aspect or embodiment described herein, the description provides a method of producing 1,2-additions on at least one of carbonyl, N=N bond, N=O bond, N=S bond, N≡C bond, P=O bond, P=S bond, or P=N bond.

In any aspect or embodiment described herein, the description provides a method of producing conjugated addition reactions on C, N, O, P, S, Si, or B.

In any aspect or embodiment described herein, the description provides a method of producing a ring opening of at least one of epoxides, aziridines, cyclopropanes, thioepoxides, iodonium, bromonium, chloronium, fluoronium, oxetanes, azetidines, cyclobutanes, and thiooxetanes.

In any aspect or embodiment described herein, the description provides a method of producing a substitution reaction on at least one of C, N, O, P, and S.

In any aspect of embodiment described herein, the description provides a method of producing an elimination reaction involving at least one of C, H, N, O, P, S, Si, B, F, Cl, Br, I, and Sn.

In any aspect or embodiment described herein, the description provides a method of producing a migration reaction involving at least one of C, H, N, O, P, S, Si, B, F, Cl, Br, I, Sn.

In any aspect or embodiment described herein, the description provides a method of producing at least one of a Diels alder reactions, an Electrocyclic reactions (Nazarov), a sigmatropic rearrangement, a dyotropic reaction, and a cycloaddition reaction.

In any aspect or embodiment described herein, the description provides a method of producing a reduction reaction or an oxidation reaction.

The preceding general areas of utility are given by way of example only and are not intended to be limiting on the scope of the present disclosure and appended claims. Additional objects and advantages associated with the compositions, methods, and processes of the present invention will be appreciated by one of ordinary skill in the art in light of the instant claims, description, and examples. For example, the various aspects and embodiments of the invention may be utilized in numerous combinations, all of which are expressly contemplated by the present description. These additional advantages objects and embodiments are expressly included within the scope of the present invention. The publications and other materials used herein to illuminate the background of the invention, and in particular cases, to provide additional details respecting the practice, are incorporated by reference, and for convenience are listed in the appended bibliography.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying drawings, which are incorporated into and form a part of the specification, illustrate several embodiments of the present invention and, together with the description, serve to explain the principles of the invention. The drawings are only for the purpose of illustrating an embodiment of the invention and are not to be construed as limiting the invention. Further objects, features and advantages of the invention will become apparent from the following detailed description taken in conjunction with the accompanying figures showing illustrative embodiments of the invention, in which.

DETAILED DESCRIPTION

Figure 1A:
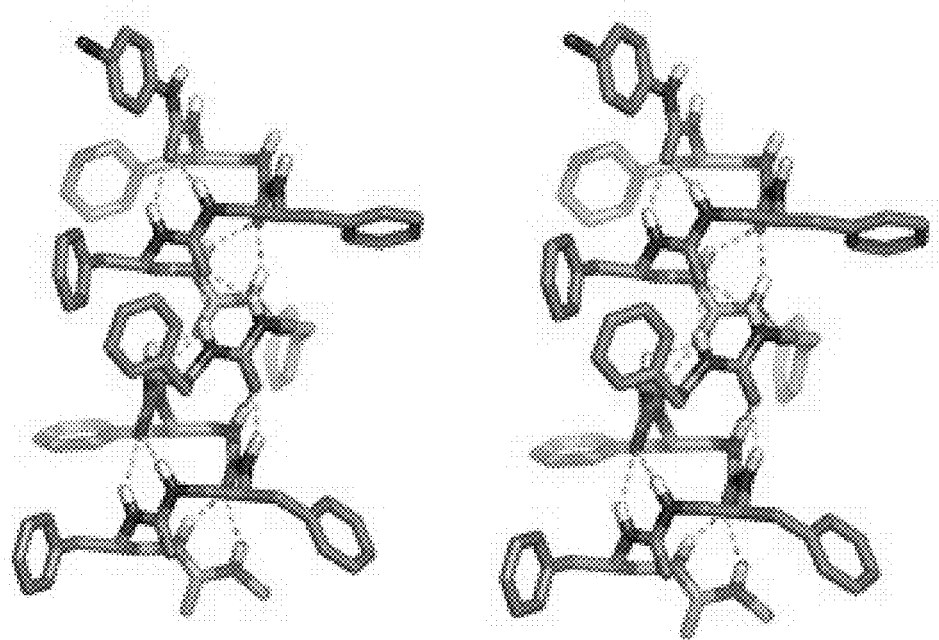
FIG. 1a A stereoview of a crystal structure of helical N,N'-linked nona-urea.
Figure 1B:
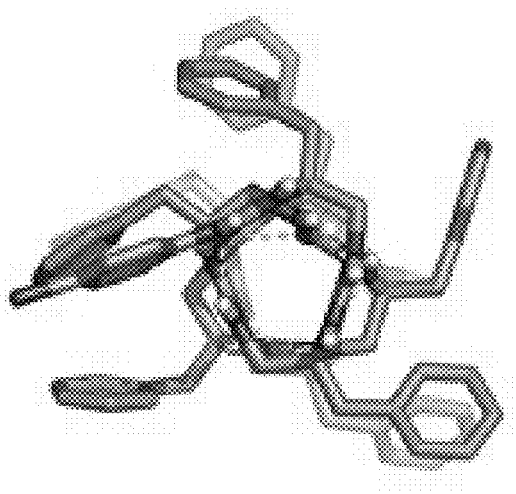
FIG. 1b Crystal structure of helical N,N' linked oligoureas viewed along the helical axis.
Figure 1C:
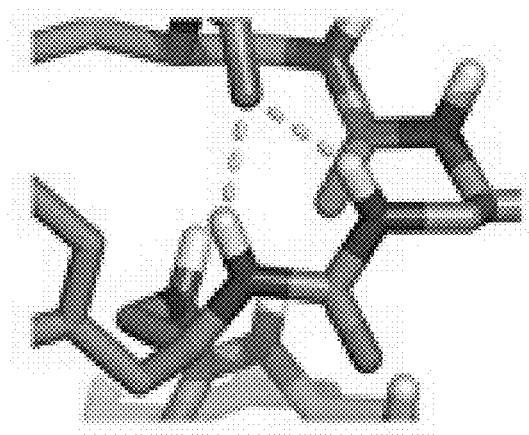
FIG. 1c Detailed structure of the three-centred H-bonding of helical N,N' linked oligoureas.

The following is a detailed description of the invention provided to aid those skilled in the art in practicing the present invention. Those of ordinary skill in the art may make modifications and variations in the embodiments described herein without departing from the spirit or scope of the present invention. Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. All publications, patent applications, patents, figures and other references mentioned herein are expressly incorporated by reference in their entirety.

In one aspect, the description provides a polar helical compound comprising an oligomer of at least 4 urea-containing residues, e.g., urea-containing peptidomimetic residues, selected from the formula (I):

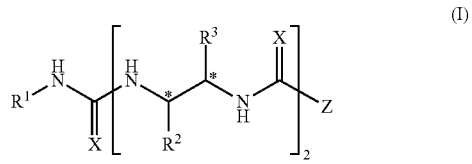

wherein X and Y are selected independently from O and S;

$R^1$ is optionally substituted alkyl, optionally substituted aryl, optionally substituted heteroaryl, optionally substituted aralkyl or optionally substituted heteroaralkyl;

$R^2$ and $R^3$ are independently selected from the group consisting of: hydrogen; any side chain of a natural amino acid; fluorine; linear, branched or cyclic C1-C6-alkyl, alkenyl or alkynyl; mono- or bicyclic aryl; mono or bicyclic heteroaryl having up to five heteroatoms selected from N, O and S; mono or bicyclic aryl-C1-C6-alkyl, alkenyl or alkynyl; trifluoromethyl; C1-C6-hydroxyle; C1-C6-alkyloxy, aryloxy, heteroaryloxy; C1-C6-alkylthio; C1-C6-amino; C1-C6-arylamino; arylamino; mono or di-C1-C6-alkylamino; mono or di-C1-C6-carboxylic acid; mono or di-C1-C6-alkylester; mono- or di-C1-C6-carboxamide; mono- or di-C1-C6-alkylcarboxamide; C1-C6-alkylsulfonamide; C1-C6-arylsulfonamide; C1-C6-sulfonamide; C1-C6-sulfamide; C1-C6-arylsulfamide C1-C6-urea; C1-C6-alkylurea; C1-C6-thiourea; C1-C6-alkylthiourea; C1-C6-guanidine; C1-C6-alkylguanidine, benzamidine, C1-C6-benzamidine; and Z is a short oligomer of at least two residues consisting of C-substituted and unsubstituted N-2-aminoethylcarbamoyl residue, C-substituted and unsubstituted N-(2-aminoethyl) carbamothioyl residues, C-substituted and unsubstituted γ-amino acid residue, —C-substituted and unsubstituted α-amino acids and any combination thereof. In a specific embodiment, the selected compound consists of a total number of 4-15 residues.

In certain aspects, $R^1$ is an optionally substituted aryl. In another aspect, $R^1$ is 3,5-bis(trifluoromethyl)benzyl.

In certain aspects, $R^1$ and $R^2$ together with the asymmetric carbon atoms to which they are attached independently defines a substituted or unsubstituted, monocyclic or bicyclic C3-C7 cycloalkyl, cycloalkenyl or heterocyclic ring optionally having one or more N, O, or S atom(s) as the heteroatom(s). More specifically, in an aspect, $R^1$ and $R^2$ together with the asymmetric carbon atoms to which they are attached independently form cyclopropane, cyclobutane, cyclopentane, or cyclohexane.

In certain aspects, Z is an alpha-peptide. In certain aspects, Z is a gamma-peptide consisting of C-substituted and unsubstituted γ-amino acid residues. In certain embodiments, Z is an N,N'-linked oligourea consisting of C-substituted and unsubstituted N-2-aminoethylcarbamoyl and/or C-substituted and unsubstituted 1,2-ethylene diamine, i.e., N-2-aminoethyl urea residues.

In a certain aspect, the compound of formula (I) is formula (II):

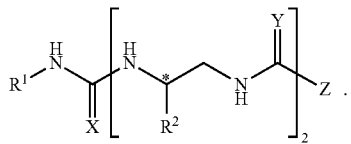
(II)

In a certain aspect, the compound of formula (II) is formula (III):

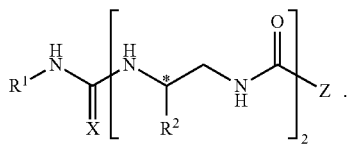
(III)

In a particular embodiment, the absolute configuration of C* of formula (II) is the same (i.e. S or R) for the two adjacent residues. In another particular embodiment, the absolute configuration of C* of formula (III) is the same (i.e. S or R) for the two adjacent residues.

In a certain aspect, the compound of formula (II) is formula (IV):

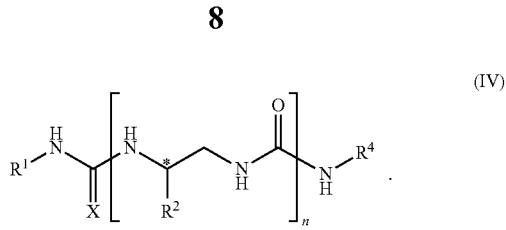
(IV)

In a certain aspect, the compound of formula (IV) is formula (V):

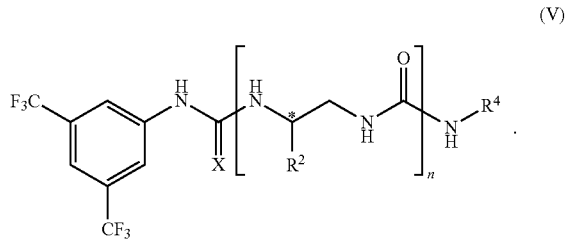
(V)

In a certain aspect, the compound of formula (IV) is formula (VI):

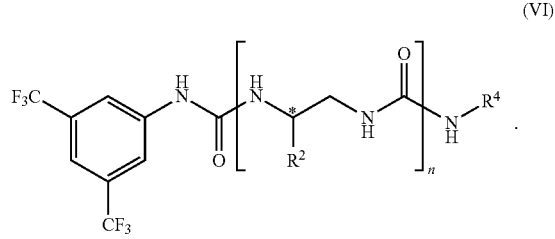
(VI)

$R^4$ is an alkyl residue in Formula IV, Formula V and Formula VI.

In certain aspects, the absolute configuration of C* of formula (IV) is the same (either S or R) for all n residues. In certain aspects, the absolute configuration of C* of formula (V) is the same (either S or R) for all n residues. In certain aspects, the absolute configuration of C* of formula (VI) is the same (either S or R) for all n residues.

In certain aspects, the Z group is covalently linked to a solid-support. In certain aspects, the solid-support is selected from the group consisting of polystyrene, silica, and polyethylene glycol resins. Solid-supported oligourea foldamer catalysts are useful because they are reusable oligourea catalysts. A solid-supported catalyst may be obtained by, for example, direct condensation of an activated urea oligomer to an amino functionalized polystyrene type support.

In any aspect or embodiment described herein, the foldamer compounds can further comprise at least one additional chemical modification. In certain embodiments, the chemical modification includes at least one of, for example, acetylation, phosphorylation, methylation, glycosylation, prenylation, isoprenylation, farnesylation, geranylation, pegylation, a disulfide bond, or combination thereof.

In an additional aspect, the description provides pharmaceutically acceptable acid and base salt forms of the foldamer compounds described herein.

The foldamers as described herein including pharmaceutically acceptable salts thereof are useful for the preparation of a medicament and/or the treatment of disease in a subject.

The compounds of the invention may optionally be administered with at least one of a pharmaceutically acceptable excipient, pharmacologically active agent or a combination thereof. As such, in an addition aspect the description provides compositions comprising an effective amount of a compound as described herein, and a pharmaceutically acceptable carrier or excipient.

The description also provides methods of treating a disease or disorder or ameliorating the effects of the same comprising the steps of administering to an individual in need thereof, a composition comprising an effective amount of a compound or salt or prodrug form thereof as described herein, and a pharmaceutically acceptable carrier or excipient, wherein the composition is effective for treating, preventing or ameliorating the effects of the disease or disorder.

In one aspect, the description provides oligomeric compounds synthesized using the methods as described herein. The description also provides pharmaceutical compositions comprising effective amounts of said compounds. In other aspects, the description provides therapeutic methods comprising the administration of an effective amount of the compounds of the invention to a mammal in need thereof.

In another aspect, the present description provides methods of using the compounds as described herein. For example, the compounds as described herein can be used as a diagnostic agent or a therapeutic agent for the treatment of a disease or condition.

In an additional aspect the present description provides methods of making compounds as described herein. Thus, in one embodiment, the present description provides for the synthesis of non-natural amino acid foldamers substituted by a wide range of functional R groups including proteinogenic side chains. In another aspect, the description provides foldamers, which comprise non-natural oligourea amino acids (i.e., an amino acid having an N, N'-linked urea bridging unit) and or peptoid versions of the same together with natural amino acids, wherein the modified peptides or foldamers form functional biopolymers.

In any aspect or embodiment described herein, the description provides a method to catalyze reactions by acid catalysis (urea) with compounds described herein.

In any aspect or embodiment described herein, the description provides a method for catalysing the addition of nucleophiles C, H, O, P, S, Si, B, F, Cl, Br, I, or Sn.

In any aspect or embodiment described herein, the description provides a method of producing 1,2-additions on at least one of a carbonyl, C=N bond, C=S bond, C=C bond, C≡C, or C≡N.

In any aspect or embodiment described herein, the description provides a method of producing 1,2-additions on at least one of carbonyl, N=N bond, N=O bond, N=S bond, N≡C bond, P=O bond, P=S bond, or P=N bond.

In any aspect or embodiment described herein, the description provides a method of producing conjugated addition reactions on C, N, O, P, S, Si, or B.

In any aspect or embodiment described herein, the description provides a method of producing a ring opening of at least one of epoxides, aziridines, cyclopropanes, thioepoxides, iodonium, bromonium, chloronium, fluoronium, oxetanes, azetidines, cyclobutanes, and thiooxetanes.

In any aspect or embodiment described herein, the description provides a method of producing a substitution reaction on at least one of C, N, O, P, and S.

In any aspect or embodiment described herein, the description provides a method of producing an elimination reaction involving at least one of C, H, N, O, P, S, Si, B, F, Cl, Br, I, and Sn.

In any aspect or embodiment described herein, the description provides a method of producing a migration reaction involving at least one of C, H, N, O, P, S, Si, B, F, Cl, Br, I, Sn.

In any aspect or embodiment described herein, the description provides a method of producing at least one of a Diels alder reactions, an Electrocyclic reactions (Nazarov), a sigmatropic rearrangement, a dyotropic reaction, and a cycloaddition reaction.

In any aspect or embodiment described herein, the description provides a method of producing a reduction reaction or an oxidation reaction.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

The following terms are used to describe the present invention. In instances where a term is not specifically defined herein, that term is given an art-recognized meaning by those of ordinary skill applying that term in context to its use in describing the present invention. The articles "a" and "an" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the 10 U.S. Patent Office Manual of Patent Examining Procedures, Section 2111.03.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a nonlimiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited. "Peptides" are typically short chains of amino acid monomers linked by peptide (amide) bonds, the covalent chemical bonds formed when the carboxyl group of one amino acid reacts with the amino group of another. The shortest peptides are dipeptides, consisting of 2 amino acids joined by a single peptide bond, followed by tripeptides, tetrapeptides, etc. A polypeptide is a long, continuous, and unbranched peptide chain.

The terms "co-administration" and "co-administering" or "combination therapy" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent, preferably at effective amounts, at the same time. In certain preferred aspects of the present invention, one or more of the present compounds described herein, are coadministered in combination with at least one additional bioactive agent. In particularly preferred aspects of the invention, the co-administration of compounds results in synergistic activity and/or therapy.

"Peptides" are typically short chains of amino acid monomers linked by peptide (amide) bonds, the covalent chemical bonds formed when the carboxyl group of one amino acid reacts with the amino group of another. The shortest peptides are dipeptides, consisting of 2 amino acids joined by a single peptide bond, followed by tripeptides, tetrapeptides, etc. A polypeptide is a long, continuous, and unbranched peptide chain.

The term "amino" or "amine" as used herein refers to —NH2 and substituted derivatives thereof wherein one or both of the hydrogens are independently replaced with 20 substituents selected from the group consisting of alkyl, haloalkyl, fluoro alkyl, alkenyl, alkynyl, carbocyclyl, heterocyclyl, aryl, aralkyl, hetero aryl, hetero aralkyl, alkylcarbonyl, haloalkylcarbonyl, carbocyclylcarbonyl, fluoroalkylcarbonyl, alkenylcarbonyl, heterocyclylcarbonyl, arylcarbonyl, alkynylcarbonyl, aralkylcarbonyl, heteroarylcarbonyl, heteroaralkylcarbonyl and the sulfonyl and sulfinyl groups defined above; or when both hydrogens together are replaced with an alkylene group (to form a ring which contains the nitrogen). Representative examples include, but are not limited to methylamino, acetylamino, and dimethylamino.

"Amino acid" refers to any molecule that contains both amino and carboxylic acid functional groups, and includes any of the naturally occurring amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D, L, or DL form. The side chains of naturally occurring amino acids are well known in the art and include, for example, hydrogen (e.g., as in glycine), alkyl (e.g., as in alanine, valine, leucine, isoleucine, proline), substituted alkyl (e.g., as in threonine, serine, methionine, cysteine, aspartic acid, asparagine, glutamic acid, glutamine, arginine, and lysine), alkaryl (e.g., as in phenylalanine and tryptophan), substituted arylalkyl (e.g., as in tyrosine), and heteroarylalkyl (e.g., as in histidine). The term is inclusive of various types of amino acids including α-, β-, γ-, or δ-amino acids, analogs and derivatives of the same, unless the context clearly indicates otherwise.

The term "amino acid sidechain" or "amino acid residue" shall mean, within context, a radical of a D- or L-amino acid sidechain (derived from an amino acid) which functions as a substituent on another group, often an alkylene (usually a methylene) group on R2' or R3' as otherwise described herein. Preferred amino acid sidechains for use in the present invention are derived from the sidechains of both natural and unnatural amino acids, preferably including, for example, alanine, β-alanine, arginine, asparagine, aspartic acid, cyclohexylalanine, cysteine, cystine, glutamic acid, glutamine, glycine, phenylalanine, histidine, isoleucine, lysine, leucine, methionine, naphthylalanine, norleucine, norvaline, proline, serine, threonine, valine, tryptophan or tyrosine, among others.

Unless the context clearly indicates otherwise, the term "any amino acid" can mean any natural or synthetic amino acid, including α-, β-, γ-, or δ-amino acids, possibly modified by the presence of one or more substituents, or combinations thereof, including analogs, derivatives, mimetics, and peptoid versions of the same. More precisely the term α-amino acid means an alpha aminated amino acid with the following general structure:

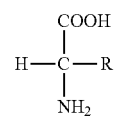

where R represents the side chain of the amino acid. In the context of the invention, R therefore represents the side chain of a side or non-side amino acid. The term "natural amino acid" means any amino acid which is found naturally in vivo in a living being. Natural amino acids therefore include amino acids coded by mRNA incorporated into proteins during translation but also other amino acids found naturally in vivo which are a product or by-product of a metabolic process, such as for example ornithine which is generated by the urea production process by arginase from L-arginine. In the invention, the amino acids used can therefore be natural or not. Namely, natural amino acids generally have the L configuration but also, according to the invention, an amino acid can have the L or D configuration. Moreover, R is of course not limited to the side chains of natural amino acid but can be freely chosen.

As used herein, "urea" or carbamide is an organic compound with the chemical formula $CO(NH_2)_2$. The molecule has two $-NH_2$ groups joined by a carbonyl ($C=O$) functional group.

Unless indicated otherwise, the term "oligourea" refers, but is in no way limited to, a residue containing N, N'-linked urea residues including oligomers of substituted or unsubstituted N-2-ethylaminocarbamoyl or 1,2-ethylene diamine residues.

The term "compound", as used herein, unless otherwise indicated, refers to any specific chemical compound disclosed herein and includes tautomers, regioisomers, geometric isomers, and where applicable, stereoisomers, including optical isomers (enantiomers) and other steroisomers (diastereomers) thereof, as well as pharmaceutically acceptable salts and derivatives (including prodrug forms) thereof where applicable, in context. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The term also refers, in context to prodrug forms of compounds which have been modified to facilitate the administration and delivery of compounds to a site of activity. It is noted that in describing the present compounds, numerous substituents and variables associated with same, among others, are described. It is understood by those of ordinary skill that molecules which are described herein are stable compounds as generally described hereunder. When the bond is shown, both a double bond and single bond are represented within the context of the compound shown.

The term "nitro" as used herein means a $-NO_2$ group.

The term "azido" as used herein means a $-N_3$ group.

The abbreviations Me, Et, Ph, Tf, Nf, Ts, Ms, Cbz, and Boc represent methyl, ethyl, phenyl, trifluoromethanesulfonyl, nonafluorobutanesulfonyl, p-toluenesulfonyl, methanesulfonyl, carbobenzyloxy, and tert-butyloxycarbonyl, respectively.

A more comprehensive list of the abbreviations utilized by organic chemists of ordinary skill in the art appears in the first issue of each volume of the Journal of Organic Chemistry; this list is typically presented in a table entitled Standard List of Abbreviations, and is incorporated herein by reference.

"Alkyl" refers to a branched or unbranched alkyl group having 1-6 carbon atoms, a branched or unbranched alkenyl group having 1-6 carbon atoms, a branched or unbranched alkinyl group having 1-6 carbon atoms. The term "alkyl" shall mean within its context a linear, branch-chained or cyclic fully saturated hydrocarbon radical or alkyl group, preferably a C1-C10, more preferably a C1-C6, alternatively a C1-C3 alkyl group, which may be optionally substituted. Examples of alkyl groups are methyl, ethyl, n-butyl, sec-butyl, n-hexyl, n-heptyl, n-octyl, n-nonyl, n-decyl, isopropyl, 2-methylpropyl, cyclopropyl, cyclopropylmethyl, cyclobutyl, cyclopentyl, cyclopentylethyl, cyclohexylethyl and cyclohexyl, among others. In certain preferred embodiments, compounds according to the present invention which may be used to covalently bind to dehalogenase enzymes. These compounds generally contain a side chain (often linked through a polyethylene glycol group) which terminates in an alkyl group which has a halogen substituent (often chlorine or bromine) on its distil end which results in covalent binding of the compound containing such a moiety to the protein.

The term "Alkenyl" refers to linear, branch-chained or cyclic C2-C10 (preferably C2-C6) hydrocarbon radicals containing at least one C=C bond. The term "Alkynyl" refers to linear, branch chained or cyclic C2-C10 (preferably C2-C6) hydrocarbon radicals containing at least one C≡C bond.

The term "unsubstituted" shall mean substituted only with hydrogen atoms. A range of carbon atoms which includes C0 means that carbon is absent and is replaced with H. Thus, a range of carbon atoms which is C0-C6 includes carbons atoms of 1, 2, 3, 4, 5 and 6 and for C0, H stands in place of carbon. The term "substituted" or "optionally substituted" shall mean independently (i.e., where more than substituent occurs, each substituent is independent of another substituent), one or more substituents (independently, up to five substituents, preferably up to three substituents, often 1 or 2 substituents on a moiety in a compound according to the present invention and may include substituents which themselves may be further substituted) at a carbon (or nitrogen) position anywhere on a molecule within context, and independently includes as substituents hydroxyl, thiol, carboxyl, cyano (C≡N), nitro ($NO_2$), halogen (preferably, 1, 2 or 3 halogens, especially on an alkyl, especially a methyl group such as a trifluoromethyl), an alkyl group (preferably, C1-C10, more preferably, C1-C6), aryl (especially phenyl and substituted phenyl for example benzyl or benzoyl), alkoxy group (preferably, C1-C6 alkyl or aryl, including phenyl and substituted phenyl), thioether (C1-C6 alkyl or aryl), acyl (preferably, C1-C6 acyl), ester or thioester (preferably, C1-C6 alkyl or aryl) including alkylene ester (such that attachment is on the alkylene group, rather than at the ester function which is preferably substituted with a C1-C6 alkyl or aryl group), preferably, C1-C6 alkyl or aryl, halogen (preferably, F or Cl), amine (including a five- or six-membered cyclic alkylene amine, further including a C1-C6 alkyl amine or a C1-C6 dialkyl amine which alkyl groups may be substituted with one or two hydroxyl groups) or an optionally substituted $-N(C0-C6$ alkyl$)C(O)(O-C1-C6$ alkyl) group (which may be optionally substituted with a polyethylene glycol chain to which is further bound an alkyl group containing a single halogen, preferably chlorine substituent), hydrazine, amido, which is preferably substituted with one or two C1-C6 alkyl groups (including a carboxamide which is optionally substituted with one or two C1-C6 alkyl groups), alkanol (preferably, C1-C6 alkyl or aryl), or alkanoic acid (preferably, C1-C6 alkyl or aryl).

The term "substituted" (each substituent being independent of another substituent) shall also mean within its context of use C1-C6 alkyl, C1-C6 alkoxy, halogen, amido, carboxamido, sulfone, including sulfonamide, keto, carboxy, C1-C6 ester (oxyester or carbonylester), C1-C6 keto, urethane $-O-C(O)-NR1R2$ or $-N(R1)-C(O)-O-R1$, nitro, cyano and amine (especially including a C1-C6 alkylene-NR1R2, a mono- or di- C1-C6 alkyl substituted amines which may be optionally substituted with one or two hydroxyl groups). Each of these groups contain unless otherwise indicated, within context, between 1 and 6 carbon atoms. In certain embodiments, preferred substituents will include for example, —NH—, —NHC(O)—, —O—,=O, —(CH2)m- (here, m and n are in context, 1, 2, 3, 4, 5 or 6), —S—, —S(O)—, SO2- or —NH—C(O)—NH—, —(CH2)nOH, —(CH2)nSH, —(CH2)nCOOH, C1-C6 alkyl, —(CH2)nO—(C1-C6 alkyl), —(CH2)nC(O)—(C1-C6 alkyl), —(CH2)nOC(O)—(C1-C6 alkyl), —(CH2)nC(O)O—(C1-C6 alkyl), —(CH2)nNHC(O)—R1, —(CH2)nC(O)—NR1R2, —(OCH2)nOH, —(CH2O)nCOOH, C1-C6 alkyl, —(OCH2)nO—(C1-C6 alkyl), —(CH2O)nC(O)—(C 1-C6 alkyl), —(OCH2)nNHC(O)—R1, —(CH2O)nC(O)—NR1R2, —S(O)2-RS, —S(O)—RS (RS is C1-C6 alkyl or a —(CH2)m-NR1R2 group), NO2, CN or halogen (F, Cl, Br, I, preferably F or Cl), depending on the context of the use of the substituent. R1 and R2 are each, within context, H or a C1-C6 alkyl group (which may be optionally substituted with one or two hydroxyl groups or up to three halogen groups, preferably fluorine). The term "substituted" shall also mean, within the chemical context of the compound defined and substituent used, an optionally substituted aryl or heteroaryl group or an optionally substituted heterocyclic group as otherwise described herein. Alkylene groups may also be substituted as otherwise disclosed herein, preferably with optionally substituted C1-C6 alkyl groups (methyl, ethyl or hydroxymethyl or hydroxyethyl is preferred, thus providing a chiral center), an amido group as described hereinabove, or a urethane group O—C(O)—NR1R2 group where R1 and R2 are as otherwise described herein, although numerous other groups may also be used as substituents. Various optionally substituted moieties may be substituted independently with 3 or more substituents, preferably no more than 3 substituents and preferably with 1 or 2 substituents. It is noted that in instances where, in a compound at a particular position of the molecule substitution is required (principally, because of valency), but no substitution is indicated, then that substituent is construed or understood to be H, unless the context of the substitution suggests otherwise.

"Hydroxyl" refers the functional group —OH when it is a substituent in an organic compound.

"Heterocycle" refers to a heterocyclic group having from 4 to 9 carbon atoms and at least one heteroatom selected from the group consisting of N, O or S, and may be aromatic (heteroaryl) or non-aromatic. Thus, the heteroaryl moieties are subsumed under the definition of heterocycle, depending on the context of its use. Exemplary heteroaryl groups are described hereinabove. Exemplary nonaromatic heterocyclic groups for use in the present invention include, for example, pyrrolidinyl, pyrrolinyl, piperidinyl, piperazinyl, N-methylpiperazinyl, imidazolinyl, pyrazolidinyl, imidazolidinyl, morpholinyl, tetrahydropyranyl, azetidinyl, oxetanyl, oxathiolanyl, pyridone, 2-pyrrolidone, ethyleneurea, 1,3 -dioxolane, 1,3-dioxane, 1,4-dioxane, phthalimide and succinimide, among others.

Heterocyclic groups can be optionally substituted with 1 to 5, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO2-alkyl, —SO2-substituted alkyl, —SO2-aryl, oxo (=O), and —SO2-heteroaryl. Such heterocyclic groups can have a single ring or multiple condensed rings. Preferred heterocyclics include morpholino, piperidinyl, and the like.

Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxy-nitrogen containing heterocycles.

"Heteroaryl" refers to a heterocyclic group having from 4 to 9 carbon atoms and at least one heteroatom selected from the group consisting of N, O or S with at least one ring of this group being aromatic. Heteroaryl groups having one or more nitrogen, oxygen, or sulfur atoms in the ring (monocyclic) such as imidazole, furyl, pyrrole, furanyl, thiene, thiazole, pyridine, pyrimidine, pyrazine, triazole, oxazole or fused ring systems such as indole, quinoline, indolizine, azaindolizine, benzofurazan, etc., among others, which may be optionally substituted as described above. Among the heteroaryl groups which may be mentioned include nitrogen containing heteroaryl groups such as pyrrole, pyridine, pyridone, pyridazine, pyrimidine, pyrazine, pyrazole, imidazole, triazole, triazine, tetrazole, indole, isoindole, indolizine, azaindolizine, purine, indazole, quinoline, dihydroquinoline, tetrahydroquinoline, isoquinoline, dihydroisoquinoline, tetrahydroisoquinoline, quinolizine, phthalazine, naphthyridine, quinoxaline, quinazoline, cinnoline, pteridine, imidazopyridine, imidazotriazine, pyrazinopyridazine, acridine, phenanthridine, carbazole, carbazoline, perimidine, phenanthroline, phenacene, oxadiazole, benzimidazole, pyrrolopyridine, pyrrolopyrimidine and pyridopyrimidine; sulfur-containing aromatic heterocycles such as thiophene and benzothiophene; oxygen-containing aromatic heterocycles such as furan, pyran, cyclopentapyran, benzofuran and isobenzofuran; and aromatic heterocycles comprising 2 or more hetero atoms selected from among nitrogen, sulfur and oxygen, such as thiazole, thiadizole, isothiazole, benzoxazole, benzothiazole, benzothiadiazole, phenothiazine, isoxazole, furazan, phenoxazine, pyrazoloxazole, imidazothiazole, thienofuran, furopyrrole, pyridoxazine, furopyridine, furopyrimidine, thienopyrimidine and oxazole, among others, all of which may be optionally substituted.

"Substituted heteroaryl" refers to a heterocyclic group having from 4 to 9 carbon atoms and at least one heteroatom selected from the group consisting of N, O or S with at least one ring of this group being aromatic and this group being substituted with one or more substituents selected from the group consisting of halogen, alkyl, carbyloxy, carbylmercapto, alkylamino, amido, carboxyl, hydroxyl, nitro, mercapto or sulfo, whereas these generic substituent group have meanings which are identical with definitions of the corresponding groups as defined in this legend.

The term "thiol" refers to the group —SH.

"Amidine" refers to a functional group that has two amine groups attached to the same carbon atom with one carbon-nitrogen double bond: HN=CR'—NH"2.

"Substituted alkyl" refers to a branched or unbranched alkyl, alkenyl or alkinyl group having 1-10 carbon atoms and having substituted by one or more substituents selected from the group consisting of hydroxyl, mercapto, carbylmercapto, halogen, carbyloxy, amino, amido, carboxyl, cycloalkyl, sulfo or acyl. These substituent generic groups having the meanings being identical with the definitions of the corresponding groups as defined herein.

"Alkylamino" denotes the group —NRfRg, where Rf and Rg, that are independent of one another, represent hydrogen, alkyl, substituted alkyl, aryl, substituted aryl, heteroaryl or substituted heteroaryl, whereas these generic substituents have meanings which are identical with definitions of the corresponding groups defined herein.

"Aryl" refers to an aromatic carbocyclic group having from 1 to 18 carbon atoms and being a substituted (as otherwise described herein) or unsubstituted monovalent aromatic radical having a single ring (e.g., benzene, phenyl, benzyl) or condensed (fused) rings, wherein at least one ring is aromatic (e.g., naphthyl, anthracenyl, phenanthrenyl, etc.) and can be bound to the compound according to the present invention at any available stable position on the ring(s) or as otherwise indicated in the chemical structure presented. Other examples of aryl groups, in context, may include heterocyclic aromatic ring systems.

"Substituted aryl" refers to an aromatic carbocyclic group having from 1 to 18 carbon atoms and being composed of at least one aromatic ring or of multiple condensed rings at least one of which being aromatic. The ring(s) are optionally substituted with one or more substituents selected from the group consisting of halogen, alkyl, hydroxyl, carbylmercapto, alkylamino, carbyloxy, amino, amido, carboxyl, nitro, mercapto or sulfo, whereas these generic substituent group have meanings which are identical with definitions of the corresponding groups as defined in this legend.

"Carboxyl" denotes the group —C(O)OR, where R is hydrogen, alkyl, substituted alkyl, aryl, substituted aryl, heteroaryl or substituted heteroaryl , whereas these generic substituents have meanings which are identical with definitions of the corresponding groups defined herein. "Cycloalkyl" refers to a monocyclic or polycyclic alkyl group containing 3 to 15 carbon atoms. "Substituted cycloalkyl" refers to a monocyclic or polycyclic alkyl group containing 3 to 15 carbon atoms and being substituted by one or more substituents selected from the group consisting of halogen, alkyl, substituted alkyl, carbyloxy, carbylmercapto, aryl, nitro, mercapto or sulfo, whereas these generic substituent groups have meanings which are identical with definitions of the corresponding groups as defined in this legend.

The term "alkenyl" refers to a monoradical of a branched or unbranched unsaturated hydrocarbon group preferably having from 2 to 40 carbon atoms, more preferably 2 to 10 carbon atoms and even more preferably 2 to 6 carbon atoms. Preferred alkenyl groups include ethenyl (—CH=CH2), n-propenyl (—CH2CH=CH2), iso-propenyl (—C(CH3)=CH2), and the like.

"Aralkyl group" refers to, for example, a C 1-C6 alkyl group which is attached to 1 or 2 aromatic hydrocarbon rings having from 6 to 10 carbon atoms and which has a total of 7 to 14 carbon atoms, such as the benzyl, alpha-naphthylmethyl, indenylmethyl, diphenylmethyl, 2-phenethyl, 2-alpha-naphthylethyl, 3-phenylpropyl, 3-alpha-naphthylpropyl, phenylbutyl, 4-alpha-naphthylbutyl or 5-phenylpentyl groups.

"Guanidine" refers generally to the amidine of amidocarbonic acid and has the general formula of: C(NH2)3.

The terms "aralkyl" and "heteroarylalkyl" refer to groups that comprise both aryl or, respectively, heteroaryl as well as alkyl and/or heteroalkyl and/or carbocyclic and/or heterocycloalkyl ring systems according to the above definitions.

EXAMPLES

Figure 2:
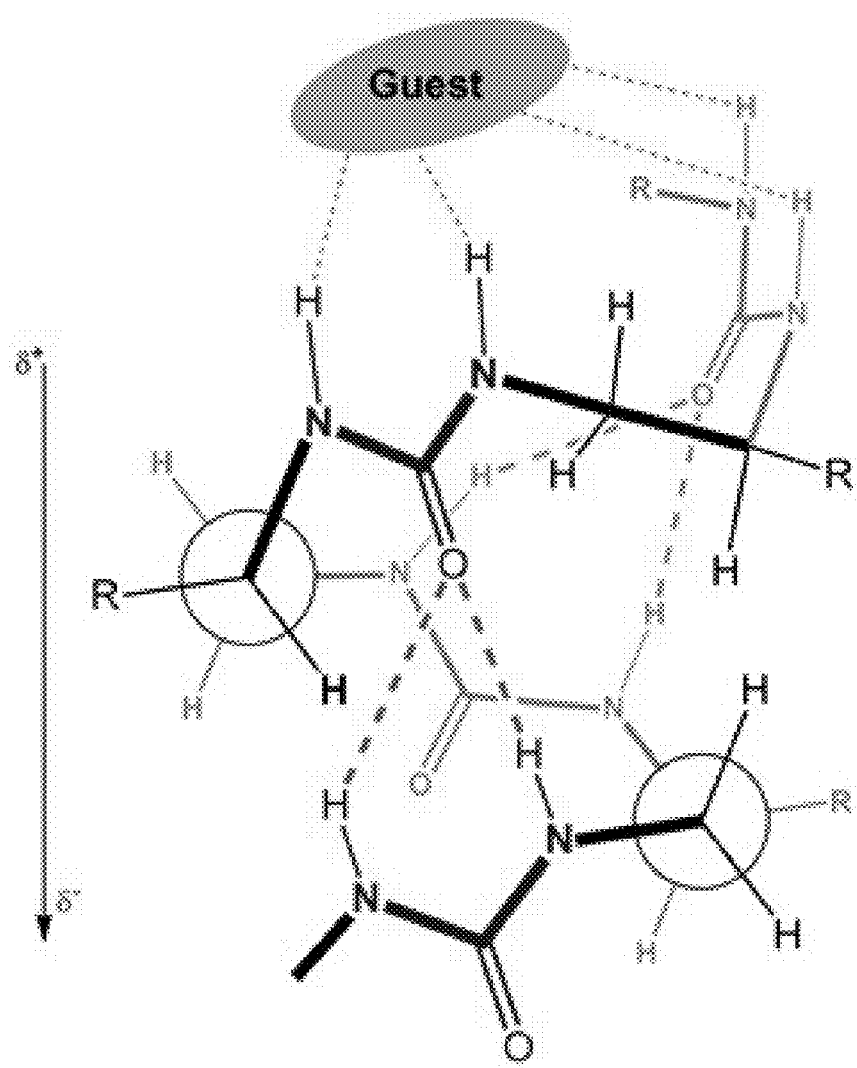
FIG. 2. Putative mode of host-guest interaction with helical oligoureas.
Figure 3A:
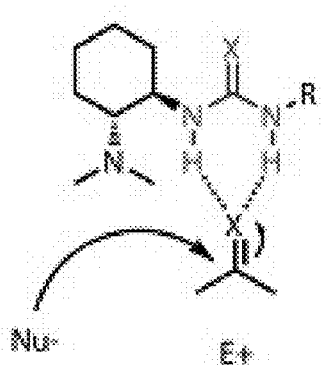
FIG. 3a. Principle of (thio)urea-based activation of a substrate by acidic hydrogens of the catalyst allowing attack by a nucleophile.
Figure 3B:
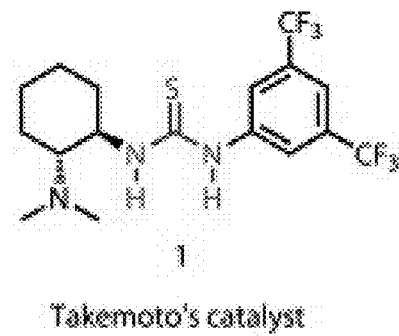
FIG. 3b. Covalent structure of bifunctional Takemoto's catalyst 1.
Figure 3C:
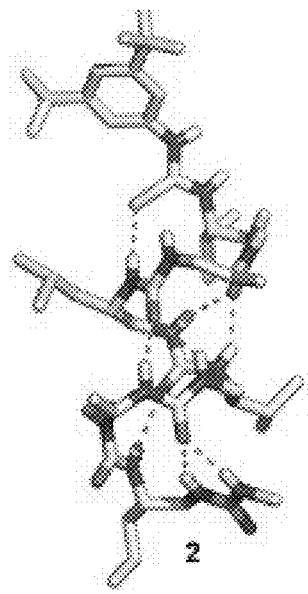
FIG. 3c. Crystal structure of 2; a representative oligo(thio)urea helical foldamer developed as a potential organocatalyst.
Figure 3D:
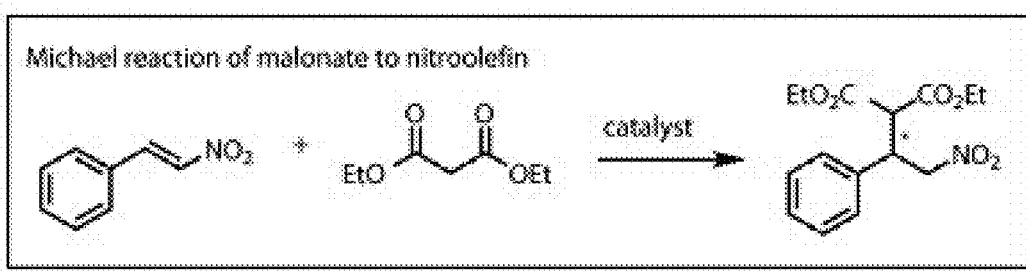
FIG. 3d. The Michael reaction of diethylmalonate to nitrostyrene.

It is believed that the well-defined 2.5-helix formed by oligoureas, and more specifically its terminal part, represents an ideal pre-organized space for specific host-guest recognition. FIG. 2 illustrates the putative mode of host-guest interaction with helical oligoureas. As shown in FIG. 2, the four NHs of the ultimate and penultimate urea groups are not involved in intramolecular H-bonding and are therefore available to interact with guest molecules. NMR spectroscopy demonstrates an interaction of various anions (oxyanions>halides) at the expected site of the helix. The proton signals corresponding to the ureas at the terminal part of the helix are the most downfield shifted upon titration with the anion (tetrabutylammonium salt). This trend demonstrates that there is likely a defined recognition site at the amino terminal end of the helix. Calculations from titration curves suggest that the affinity and the binding mode may be modulated by the nature of the capping group (alkyl carbamate, alkyl urea, aryl urea with electron withdrawing groups, thiourea, etc.).

The Michael reaction of 1,3-dicarbonyl compounds (e.g. malonates) to nitroolefins has been shown previously to be catalyzed by simple thiourea derivatives (FIG. 3a-3d). The Michael reaction of nitroolefins represents a convenient access to nitroalkanes that are versatile intermediates in organic synthesis. The nitro functionality can be easily transformed into amino group, for example, providing a wide range of synthetically interesting (i.e. bioactive) compounds including γ-amino acids (e.g. Lyrica intermediate). FIG. 3a-3d illustrates the principle of (thio)urea-based activation of a substrate by acidic hydrogens of the catalyst allowing attack by a nucleophile.

An enantioselective version of the Michael reaction has been reported, where a bifunctional catalyst with (R,R)-1, 2-cyclohexyldiamine as a chiral scaffold (i.e. Takemoto's catalyst 1 shown in FIG. 3b) was developed. This bifunctional catalyst which contains both a thiourea moiety and an amino group is able in nonpolar solvents to activate both the nitroolefin and the nucleophile simultaneously and can control the approach of the nucleophile to the nitroolefin leading to addition products with excellent stereoselectivities. The drawback of the approach is that relatively high load of catalysts (typically 10 mol %) are needed and that the tertiary base necessary to deprotonate the 1,3-dicarbonyl compound cannot be disconnected from the catalyst.

In one aspect, oligourea foldamers are used as catalysts. In certain embodiments, the oligourea foldamers includes an aromatic urea or thiourea termination bearing electron withdrawing groups (3,5-bis(trifluoromethyl)benzene). The crystal structure of the hexa(thio)urea oligomer 2, a representative urea foldamer in the series is shown in FIG. 3a-3d and reveals that the thiocarbonyl group is intramolecularly H-bonded to urea NHs. Tables 1 and 2 compare the catalytic activity of hexa(thio)urea oligomer 2 with that of Takemoto's catalyst 1.

TABLE 1

Michael Reaction of nitrostyrene with Takemoto's catalyst and with oligourea catalyst 2.

| Catalyst | Catalyst (mol %) | T (° C.) | time | Base (%) | Conversion (NMR, %)$^a$ | Isolated yield (%)$^b$ | ee (%)$^c$ |
|---|---|---|---|---|---|---|---|
| — | — | rt | 24 h | Et$_3$N (10) | 11 | — | — |
| 1 | 10 | rt | 24 h | — | >95 | 82 (86)$^d$ | 82 (93)$^d$ |
| 1 | 0.1 | rt | 24 h | Et$_3$N (10) | 20% | ND$^e$ | 15 |

TABLE 1-continued

Michael Reaction of nitrostyrene with Takemoto's catalyst and with oligourea catalyst 2.

| Catalyst | Catalyst (mol %) | T (° C.) | time | Base (%) | Conversion (NMR, %)$^a$ | Isolated yield (%)$^b$ | ee (%)$^c$ |
|---|---|---|---|---|---|---|---|
| 2 | 1 | rt | 24 h | Et$_3$N (10) | ≥95 | 85 | 84 |
| 2 | 1 | 4° C. | 24 h | Et$_3$N (10) | ≥95 | 85 | 89 |
| 2 | 1 | −20° C. | 24 h | Et$_3$N (10) | 95 | 85 | 93 |
| 2 | 0.5 | −20° C. | 24 h | Et$_3$N (10) | 94 | 84 | 94 |
| 2 | 0.25 | −20° C. | 24 h | Et$_3$N (10) | 90 | 82 | 92 |
| 2 | 0.1 | −20° C. | 48 h | Et$_3$N (10) | 90 | 82 | 91 |

$^a$Conversion was determined by $^1$H NMR from the ratio of the product to starting material;
$^b$Isolated yield of analytically pure material after chromatography.
$^c$Enantiomeric excess was determined by chiral HPLC;
$^d$The values in bracket are those reported by Takemoto and coworkers;
$^e$not determined The hexa(thio)urea oligomer catalyst 2 is as efficient as Takemoto's catalyst 1 even when used at 1 mol % and despite the fact that the tertiary amino group for malonate activation is separated from the catalyst. This is in sharp contrast with Takemoto's catalyst 1 in which the thiourea and the tertiary amino group are both needed in the catalyst structure for high yield and selectivity. Under atmospheric conditions, Takemoto's catalyst (bought from Sigma-Aldrich) was found to give enantioselectivity values significantly lower than values found in the literature (see Table 1). The reaction catalyzed by the hexa(thio)urea oligomer 2 proceeded with good conversion and higher enantioselectivity (93% ee) at lower temperature (−20° C.). In addition, the catalyst load can be further decreased. At 0.1 mol % of hexa(thio)urea oligomer 2, both the conversion and enantioselectivity remained excellent (90% and 91% ee), as compared to the 10 mol % of Takemoto's catalyst 1.

TABLE 2

Identification of optimal reaction conditions at 0.1 mol % of oligourea catalyst 2.$^a$

| Catalyst | Catalyst (mol %) | [Nitroolefin] mM | solvent | Base (%) | Conversion (NMR, %)$^b$ | Isolated yield (%)$^c$ | ee (%)$^d$ |
|---|---|---|---|---|---|---|---|
| 2 | 0.1 | 0.5 | toluene | Et$_3$N (10) | 90 | 82 | 91 |
| 2 | 0.1 | 0.5 | toluene | Et$_3$N (5) | 75 | 67 | 90 |
| 2 | 0.1 | 0.5 | toluene | Et$_3$N (1) | 18 | — | 50 |
| 2 | 0.1 | 0.5 | toluene | Et$_3$N (15) | 93 | 85 | 93 |
| 2 | 0.1 | 0.5 | toluene | Et$_3$N (20) | 95 | 87 | 92 |
| 2 | 0.1 | 0.66 | toluene | Et$_3$N (10) | 99 | 82 | 93 |
| 2 | 0.1 | 0.66 | CCl$_4$ | Et$_3$N (10) | ≥95 | nd$^e$ | 94 |
| 2 | 0.1 | 0.66 | toluene | DIMA$^f$ (10) | 95 | nd | 95 |
| 2 | 0.1 | 0.66 | toluene | DEMA$^g$ (10) | 90 | nd | 90 |
| 2 | 0.1 | 0.66 | toluene | NMP$^h$ (10) | 80 | nd | 86 |

$^a$reactions were performed for 48 h at −20° C.
$^b$Conversion was determined by $^1$H NMR from the ratio of the product to starting material;
$^c$Isolated yield of analytically pure material after chromatography.
$^d$Enantiomeric excess was determined by chiral HPLC.
$^e$not determined;
$^f$diisopropylmethylamine;
$^g$diethylmethylamine;
$^h$N-methylpiperidine Conditions at 0.1 mol % of hexa(thio)urea oligomer 2 have been further analyzed by varying the concentration of the reaction, the amount and the nature of the tertiary amine and the polarity of the solvent. The results are summarized in Table 2. Increasing the amount of tertiary amine (Et$_3$N) results in an improvement on both conversion and enantioselectivity. In contrast, the reactivity was significantly reduced at Et$_3$N concentration below 10%. Improvement is also observed at higher concentration of nitroolefin and in a nonpolar solvent such as CCl$_4$. Significant results have been obtained upon screening tertiary amines with slightly different pKa values. The best results were obtained with Diisopropylmethylamine (DIMA) which gave the expected adduct in high yield (95%) and excellent enantioselectivity (95% ee).

Figure 4:
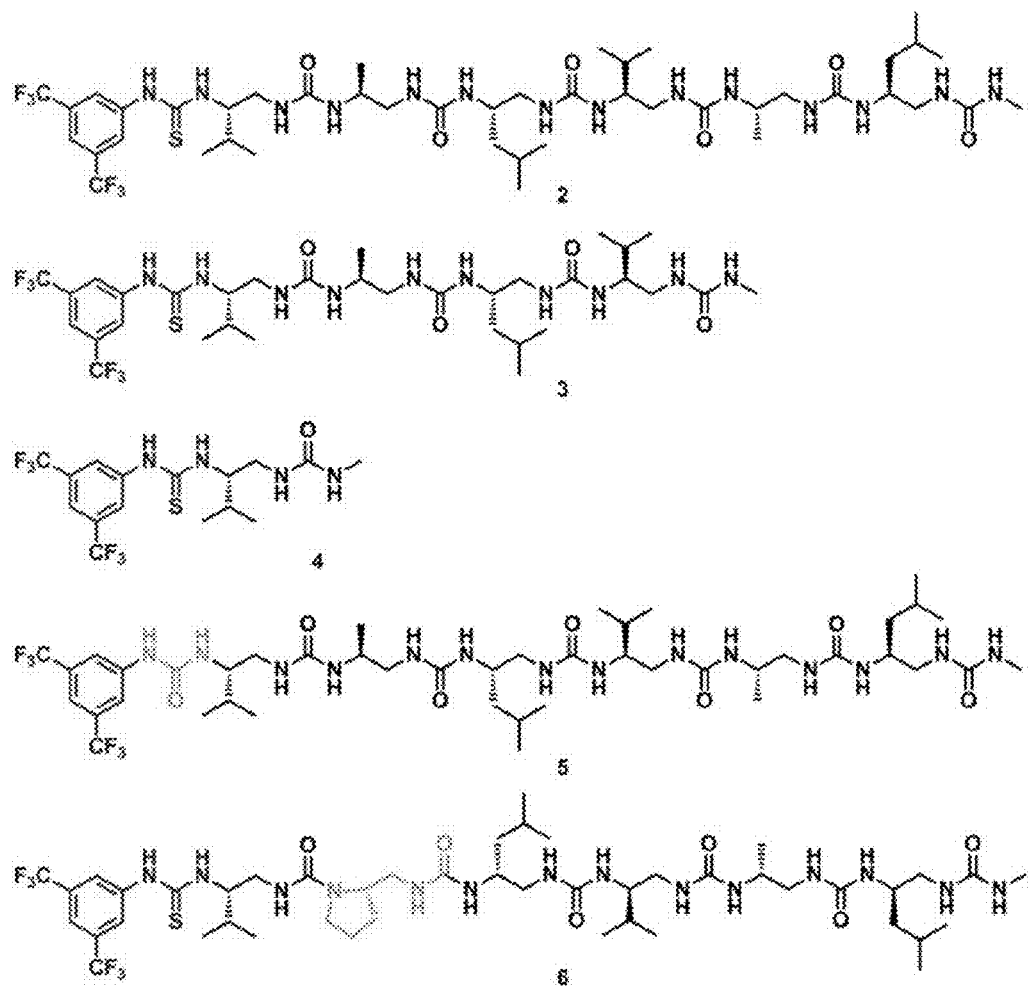
FIG. 4. Formulae of 4 additional oligomer catalysts; oligomer catalysts 3-6 are analogues of oligomer catalyst 2.

FIG. 4 illustrates the formulae of four additional oligourea oligomer catalysts. Oligourea oligomer catalysts 3 and 4 are shorter versions of oligourea oligomer catalyst 2 (respectively only four and one residue instead of six); oligourea oligomer catalysts 5 has a urea termination (instead of a thiourea); oligourea oligomer 6 has a pyrrolidine residue at the penultimate position which blocks the second accessible urea moiety.

Table 3 summaries how well oligourea oligomers 2-6 function as catalysts in the Michael Reaction. Oligourea oligomers with a longer chain length have greater conversion and higher enantioselectivity (2>3>4). While not to be held to any particular theory, it is believed that a stable helical conformation is needed for efficient catalysis. The introduction of a pyrrolidine residue in oligourea oligomer 6 appears to be detrimental for catalytic activity thereby suggesting that the second urea site may be required for efficient catalysis.

TABLE 3

Identification of optimal reaction conditions at 0.1 mol % of catalyst 2$^a$

| Catalyst | Catalyst (mol %) | [Nitroolefin] mM | solvent | Base (%) | Conversion (NMR, %)$^b$ | Isolated yield (%)$^c$ | ee (%)$^d$ |
|---|---|---|---|---|---|---|---|
| 2 | 0.1 | 0.66 | toluene | Et$_3$N (10) | 99 | 82 | 93 |
| 3 | 0.1 | 0.66 | toluene | Et$_3$N (10) | 75 | 75 | 80 |

TABLE 3-continued

Identification of optimal reaction conditions at 0.1 mol % of catalyst 2[a]

| Catalyst | Catalyst (mol %) | [Nitroolefin] mM | solvent | Base (%) | Conversion (NMR, %)[b] | Isolated yield (%)[c] | ee (%)[d] |
|---|---|---|---|---|---|---|---|
| 4 | 0.1 | 0.66 | toluene | Et₃N (10) | 10 | nd[e] | 11 |
| 5 | 0.1 | 0.66 | toluene | Et₃N (10) | 91 | 86 | 92 |
| 6 | 0.1 | 0.66 | toluene | Et₃N (10) | 12 | nd[e] | nd[e] |

[a]reactions were performed for 48 h at −20° C.
[b]Conversion was determined by ¹H NMR from the ratio of the product to starting material;
[c]Isolated yield of analytically pure material after chromatography.
[d]Enantiomeric excess was determined by chiral HPLC.
[e]not determined Thioureas have been employed more than the corresponding ureas to perform organocatalyzed reaction due to an increase of the NH acidity. The impact of this structural change on the catalytic activity of the helical foldamer is shown in Table 4. More specifically, oligomer catalysts 2 and 5 bearing respectively terminal thiourea and urea functions were compared. The efficiency of both catalysts was evaluated at different temperatures (−20° C., 0° C., 20° C.) and after either 24 h or 48 h reaction time.

TABLE 4

Comparison between catalysts 2 and 5.

| Catalyst | Time | Temperature (° C.) | Loading (mol %) | Conversion (NMR, %) | Isolated yield (%) | ee (%) |
|---|---|---|---|---|---|---|
| 2 | 48 h | −20 | 0.1 | 99 | 82 | 93 |
| 5 | 48 h | −20 | 0.1 | 100 | 80 | 95 |
| 2 | 48 h | 0 | 0.1 | 99 | 76 | 90 |
| 5 | 48 h | 0 | 0.1 | 100 | 76 | 91 |
| 2 | 48 h | 20 | 0.1 | 98 | 71 | 87 |
| 5 | 48 h | 20 | 0.1 | 100 | 74 | 89 |
| 2 | 24 h | −20 | 0.1 | 94 | 59 | 88 |
| 5 | 24 h | −20 | 0.1 | 99 | 63 | 94 |
| 2 | 24 h | 0 | 0.1 | 98 | 72 | 91 |
| 5 | 24 h | 0 | 0.1 | 99 | 73 | 92 |
| 2 | 24 h | 20 | 0.1 | 94 | 73 | 86 |
| 5 | 24 h | 20 | 0.1 | 98 | 68 | 88 |

Unexpectedly, the urea-catalyst 5 gave similar or even slightly better results than thiourea-catalyst 2 under all reaction conditions tested. Not to be held to any particular theory, it is believed increase of acidity connected to the insertion of the thiourea function may be counterbalanced by the orientation modification of the thiourea function. This conformational change might destabilize at the transition state the optimal organization of the substrates around the catalyst.

Figure 5:
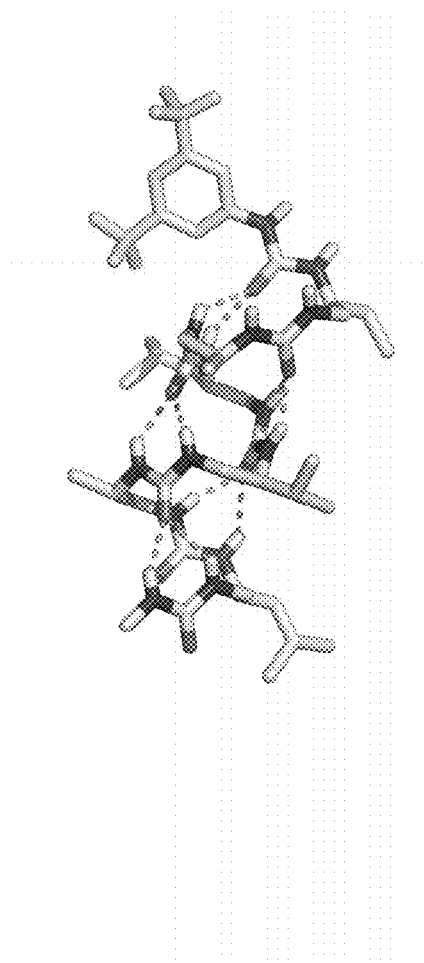
FIG. 5. Crystal structure of oligourea helical foldamer 5 developed as an analogue of catalyst 2.

Tables 4-6 highlight the potential of the urea termination in oligourea catalyst 5, which is as effective and even superior to the thiourea termination in catalyst 2. This is a very useful addition to oligourea catalysis. Moreover, urea derivatives are easier to synthetize and to purify than the corresponding thiourea oligomeric derivatives. As a consequence, catalyst 5 (see X-ray structure in FIG. 5) was used to study further the potential of the oligoureas as organocatalysts in synthetic chemistry.

The strength of the interaction between the catalyst and the substrates, as well as the stability of the catalyst conformation, is examined in Table 5 by progressively increasing the temperature of the reaction mixture from −20° C. to 80° C. The enantiomeric excess progressively decreased when the temperature of the reaction mixture increased. In spite of a temperature of 80° C., a 85:15 ratio between the two enantiomers was observed indicating the robustness of the studied catalytic system. This feature could be particularly interesting for reactions which need high temperature to occur.

TABLE 5

Impact of the temperature.

| Catalyst | Catalyst (mol %) | T (° C.) | Conversion (NMR, %) | Isolated yield (%) | ee (%) |
|---|---|---|---|---|---|
| 5 | 0.1 | −20 | 100 | 80 | 95 |
| 5 | 0.1 | 0 | 100 | 75 | 91 |
| 5 | 0.1 | 20 | 100 | 74 | 89 |
| 5 | 0.1 | 40 | 100 | 72 | 82 |
| 5 | 0.1 | 60 | 100 | 85 | 76 |
| 5 | 0.1 | 80 | 100 | 77 | 69 |

Table 6 examines the impact of the catalyst loading on the reaction. Decreasing the catalyst loading from 0.1 mol % to 0.01 mol % did not affect significantly the yield and the enantioselectivity of the reaction. At 0.01 mol % which is 2 or 3 orders of magnitude lower than loading classically employed in organocatalysis, the product was isolated with 81% yield and 92% ee. These results indicate the efficiency of the oligourea catalyst as well as the strength of the interactions between the different partners involved in the catalytic system.

TABLE 3

Impact of the catalyst loading.

| Catalyst | Catalyst (mol %) | T (° C.) | Conversion (NMR, %) | Isolated yield (%) | ee (%) |
|---|---|---|---|---|---|
| 5 | 0.1 | −20 | 100 | 85 | 95 |
| 5 | 0.05 | −20 | 100 | 85 | 94 |
| 5 | 0.01 | −20 | 98 | 81 | 92 |

Overall this last series of results at (very) low catalyst loading confirm the potential and the precision of urea-foldamer catalysis, suggesting that the helical conformation and the access to two urea sites may be required for effective catalysis.

A representative procedure for the catalysis with oligourea catalyst 5 is shown in FIG. 6 and described below.

| nitrostyrene | 100 mg | 1 eq | 0.67 mmol |
| diethyl malonate | 204 µL | 2 eq | 1.34 mmol |
| catalyst | from stock solution | 0.1% eq | 6.7 × 10⁻⁴ mmol |
| Et₃N | from stock solution | 10% eq | 6.7 × 10⁻² mmol |

Catalyst 5 (12 mg) was dissolved in 1:1 mixture of DCM/MeOH (5.8 mL) (HPLC quality) and a vial was charged with this 2 mM catalyst solution (335 µL, 6.7×10⁻⁴ mmol, 0.001 eq). After evaporation of the solvents under reduced pressure, the catalyst was dried overnight under high vacuum. To the vial containing the catalyst 5 was added nitrostyrene (100 mg, 0.67 mmol, 1 eq) and the mixture was dissolved in 670 µL of a stock solution of Et₃N (139 µL) in toluene (10 mL). After homogenization by sonication, diethyl malonate (204 μL, 1.34 mmol, 2 eq) was added. The reaction mixture was then allowed to react at −20° C. (freezer, without stirring). At the end of the experiment, the reaction mixture was quenched with 1N $KHSO_4$ (20 mL) and the aqueous layer was extracted with diethyl ether (3×20 mL). The organic layer was washed with brine (1×20 mL) and re-extracted with $Et_2O$ (1×20 mL). The combined organic layers were dried over $MgSO_4$, filtered then concentrated under reduced pressure. The crude was purified on Silica Gel Column Chromatography (toluene liquid loading, eluent: cyclohexane/EtOAc, from 97:3 to 93:7) to furnish the tilted compound as a colourless oil which might crystalize.

Conversion was determined by $^1H$ NMR in $CDCl_3$ at 300 MHz considering the malonic proton of the product (3.83 ppm, d, 1H) and the most unshielded ethylenic proton of nitrostyrene (8.11 ppm, d, 1H).

Enantiomeric excess was determined by Chiral HPLC, (IA column, Hexane:Isopropanol 8:2, UV detection at 254 nm, injected sample: $10^{-2}M$, $t_R$=8.5 min (S), $t_R$=18.4 min (R)). Embodiments of the disclosure are effective catalysts at very low loading.

Pharmaceutical Forms

The chimeric compounds as described herein including pharmaceutically acceptable salts thereof are useful for the preparation of a medicament and/or the treatment of disease in a subject. In the case where a salt of a compound is desired and the compound is produced in the form of the desired salt, it can be subjected to purification as such. In the case where a compound is produced in the free state and its salt is desired, the compound is dissolved or suspended in a suitable organic solvent, followed by addition of an acid or a base to form a salt. As such, in an addition aspect the description provides compositions comprising an effective amount of a peptide-oligourea chimera as described herein, and a pharmaceutically acceptable carrier or excipient.

The compounds of the invention may optionally be administered with at least one of a pharmaceutically acceptable excipient, pharmacologically active agent or a combination thereof. These novel, unnatural peptidomimetics are resistant or wholly immune to peptidase and protease degradation and are conformationally restrained. Thus, they are useful as tools to model peptide and protein conformations in aqueous solutions. The compounds are also useful as non-enzymatically degradable probes to mimic protein behavior in solution. As such, the description further provides the compositions comprising an effective amount of a chimeric compound as described herein, and a pharmaceutically acceptable carrier or excipient.

Certain compounds of the invention and their salts may exist in more than one crystal form and the present invention includes each crystal form and mixtures thereof. Certain compounds of the invention and their salts may also exist in the form of solvates, for example hydrates, and the present invention includes each solvate and mixtures thereof.

Certain compounds of the invention may contain one or more chiral centers, and exist in different optically active forms. When compounds of the invention contain one chiral center, the compounds exist in two enantiomeric forms and the present invention includes both enantiomers and mixtures of enantiomers, such as racemic mixtures. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step may be used to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound of the invention contains more than one chiral center, it may exist in diastereoisomeric forms. The diastereoisomeric compounds may be separated by methods known to those skilled in the art, for example chromatography or crystallization and the individual enantiomers may be separated as described above. The present invention includes each diastereoisomer of compounds of the invention and mixtures thereof.

Certain compounds of the invention may exist in different tautomeric forms or as different geometric isomers, and the present invention includes each tautomer and/or geometric isomer of compounds of the invention and mixtures thereof.

Certain compounds of the invention may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of the invention and mixtures thereof.

Certain compounds of the invention may exist in zwitterionic form and the present invention includes each zwitterionic form of compounds of the invention and mixtures thereof.

The present disclosure encompasses all possible isomers including tautomers and mixtures thereof. Where chiral carbons lend themselves to two different enantiomers, both enantiomers are contemplated as well as procedures for separating the two enantiomers.

The present invention also relates to pharmaceutically acceptable salts, racemates, and optical isomers thereof. The compounds of this invention typically contain one or more chiral centers. Accordingly, this invention is intended to include racemic mixtures, diasteromers, enantiomers and mixture enriched in one or more stereoisomer. The scope of the invention as described and claimed encompasses the racemic forms of the compounds as well as the individual enantiomers and non-racemic mixtures thereof.

Many of the compounds of the invention may be provided as salts with pharmaceutically compatible counter ions (i.e., pharmaceutically acceptable salts).

The term "pharmaceutically acceptable salt" is used throughout the specification to describe, where applicable, a salt form of one or more of the compounds or prodrugs described herein which are presented to increase the solubility of the compound in the gastric juices of the patient's gastrointestinal tract in order to promote dissolution and the bioavailability of the compounds. Pharmaceutically acceptable salts include those derived from pharmaceutically acceptable inorganic or organic bases and acids, where applicable. Suitable salts include those derived from alkali metals such as potassium and sodium, alkaline earth metals such as calcium, magnesium and ammonium salts, among numerous other acids and bases well known in the pharmaceutical art. Sodium and potassium salts are particularly preferred as neutralization salts of the phosphates according to the present invention. In a preferred embodiment, the description provides pharmaceutically acceptable salts of the modified peptides as described herein, which retain the biological effectiveness and properties of the parent compounds and which are not biologically or otherwise harmful as the dosage administered. The compounds of this invention are capable of forming both acid and base salts by virtue of the presence of amino and carboxy groups respectively.

A "pharmaceutically acceptable counterion" is an ionic portion of a salt that is not toxic when released from the salt upon administration to a recipient. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free base forms.

Acids commonly employed to form pharmaceutically acceptable salts include inorganic acids such as hydrogen bisulfide, hydrochloric, hydrobromic, hydroiodic, sulfuric and phosphoric acid, as well as organic acids such as para-toluenesulfonic, salicylic, tartaric, bitartaric, ascorbic, maleic, besylic, fumaric, gluconic, glucuronic, formic, glutamic, methanesulfonic, ethanesulfonic, benzenesulfonic, lactic, oxalic, parabromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, sub erate, sebacate, fumarate, maleate, butyne-I,4-dioate, hexyne-I,6-dioate, benzoate, chlorobenzoate, methylbenzoate, dinitrobenzoate, hydroxybenzoate, methoxybenzoate, phthalate, terephthalate, sulfonate, xylenesulfonate, phenylacetate, phenylpropionate, phenylbutyrate, citrate, lactate, --hydroxybutyrate, glycolate, maleate, tartrate, methanesulfonate, propanesulfonate, naphthalene-I-sulfonate, naphthalene-2-sulfonate, mandelate and the like salts.

Preferred pharmaceutically acceptable acid addition salts include those formed with mineral acids such as hydrochloric acid and hydrobromic acid, and especially those formed with organic acids such as maleic acid. Suitable bases for forming pharmaceutically acceptable salts with acidic functional groups include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-Iower alkyl amines), such as mono-, bis-, or tris-(2-hydroxyethyl)amine, 2-hydroxy-tert-butylamine, or tris-(hydroxymethyl)methylamine, N,N-di-lower alkyl-N (hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like.

Prodrugs

The descriptoin also provides prodrug forms of the above described oligomeric compounds, wherein the prodrug is metabolized in vivo to produce an analog or derivative as set forth above. Indeed, some of the described compounds may be a prodrug for another analog or derivative. The term "prodrug" is well understood in the art and refers to an agent which is converted into the parent drug in vivo by some physiological chemical process (e.g., a prodrug on being brought to the physiological pH is converted to the desired drug form). For example, see Remington's Pharmaceutical Sciences, 1980, vol. 16, Mack Publishing Company, Easton, Pa., 61 and 424.

Pro-drugs are often useful because, in some situations, they may be easier to administer than the parent drug. They may, for instance, be bioavailable by oral administration whereas the parent drug is not. The prodrug may also have improved solubility in pharmacological compositions over the parent drug. An example, without limitation, of a prodrug would be a compound of the present invention wherein it is administered as an ester (the "pro-drug") to facilitate transmittal across a cell membrane where water solubility is not beneficial, but then it is metabolically hydrolyzed to the carboxylic acid once inside the cell where water solubility is beneficial. Pro-drugs have many useful properties. For example, a pro-drug may be more water soluble than the ultimate drug, thereby facilitating intravenous administration of the drug. A pro-drug may also have a higher level of oral bioavailability than the ultimate drug. After administration,the prodrug is enzymatically or chemically cleaved to deliver the ultimate drug in the blood or tissue.

Exemplary pro-drugs upon cleavage release the corresponding free acid, and such hydrolyzable ester-forming residues of the compounds of this invention include but are not limited to carboxylic acid substituents (e.g., —C(O)2H or a moiety that contains a carboxylic acid) wherein the free hydrogen is replaced by (C1-C4)alkyl, (C1-C12)alkanoyloxymethyl, (C4-C9)1-(alkanoyloxy)ethyl, I-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, I-methyl-1-10 (alkoxycarbonyloxy)ethyl having from 5 to 8 carbon atoms, N-(alkoxycarbonyl)aminomethyl having from 3 to 9 carbon atoms, 1-(N-(alkoxycarbonyl) amino) ethyl having from 4 to 10 carbon atoms, 3-phthalidyl, 4-crotonolactonyl, gamma-butyrolacton-4-yl, di-N,N-(C1-C2)alkylamino(C2-C3)alkyl (such as --dimethylaminoethyl), carbamoyl-(C1-C2)alkyl, N,N-die C1-C2)-alkylcarbamoyl-(C1-15 C2)alkyl and piperidino-, pyrrolidino- or morpholino(C2-C3)alkyl.

Other exemplary pro-drugs release an alcohol or amine of a compound of the invention wherein the free hydrogen of a hydroxyl or amine substituent is replaced by (C1-C6) alkanoyloxymethyl, 1-((C1-C6)alkanoyloxy)ethyl, I-methyl-1-((C1-C6)alkanoyloxy)ethyl, (C1-C6)alkoxycarbonyl-oxymethyl, N—(C1-C6)alkoxycarbonylamino- 20 methyl, succinoyl, (C1-C6)alkanoyl, a-amino(C1-C4)alkanoyl, arylactyl and a-aminoacyl, or a-aminoacyl-a-aminoacyl wherein said a-aminoacyl moieties are independently any of the naturally occurring L-amino acids found in proteins, —P(O)(OH)2'-P(O)(O(C1-C6)alkyl)2 or glycosyl (the radical resulting from detachment of the hydroxyl of the hemiacetal of a carbohydrate).

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. Protective 30 Groups in Organic Synthesis, 2nd ed.; Wiley: N.Y., 1991). Protected forms of the inventive compounds are included within the scope of this invention.

The term "chemically protected form," as used herein, pertains to a compound in which one or more reactive functional groups are protected from undesirable chemical reactions, that is, are in the form of a protected or protecting group (also known as a masked or masking group). It may be convenient or desirable to prepare, purify, and/or handle the active compound in a chemically protected form.

By protecting a reactive functional group, reactions involving other unprotected reactive functional groups can be performed, without affecting the protected group; the protecting group may be removed, usually in a subsequent step, without substantially affecting the remainder of the molecule. See, for example, Protective Groups in Organic Synthesis (T. Green and P. Wuts, Wiley, 1991), and Protective Groups in Organic Synthesis (T. Green and P. Wuts; 3rd Edition; John Wiley and Sons, 1999).

For example, a hydroxy group may be protected as an ether (—OR) or an ester (—OC(=O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(=O)CH3, —OAc). For example, an aldehyde or ketone group may be protected as an acetal or ketal, respectively, in which the carbonyl group (C(=O)) is converted to a diether (C(OR)2), by reaction with, for example, a primary alcohol. The aldehyde or ketone group is readily regenerated by hydrolysis using a large excess of water in the presence of acid. For example, an amine group may be protected, for example, as an amide (—NRC(=O)R) or a urethane (—NRC(=O)OR), for example, as: a methyl amide (—NHC(=O)CH3); a benzyloxy amide (—NHC(=O)OCH2C6HsNHCbz); as a t-butoxy amide (NHC=(=O)OC(CH3)3, —NHBoc); a 2-biphenyl-2-propoxy amide (NHC(=O)OC(CH3)2C6H4C6HsNHBoc), as a 9-fluorenylmethoxy amide (—NHFmoc), as a 6-nitroveratryloxy amide (—NHNvoc), as a 2-trimethylsilylethyloxy amide (—NHTeoc), as a 2,2,2-trichloroethyloxy amide (—NHTroc), as an allyloxy amide (—NHAlloc), as a 2-(phenylsulfonyl)ethyloxy amide (—NHPsec); or, in suitable cases (e.g., cyclic amines), as a nitroxide radical.

For example, a carboxylic acid group may be protected as an ester or an amide, for example, as: a benzyl ester; a t-butyl ester; a methyl ester; or a methyl amide. For example, a thiol group may be protected as a thioether (—SR), for example, as: a benzyl thioether; or an acetamidomethyl ether (—SCH2NHC(=O)CH3). In at least certain examples, the compounds disclosed herein can be used in the treatment of disorders associated with pathogen infection. Disorders associated with infection by pathogens include, but are not limited to, infection by viruses (DNA viruses, RNA viruses, animal viruses, and the like), bacteria (e.g., gram positive bacteria, gram negative bacteria, acid-fast bacteria, and the like), fungi, parasitic microbes, nematodes, and the like.

The term "pharmaceutically acceptable derivative" is used throughout the specification to describe any pharmaceutically acceptable prodrug form (such as an ester, amide other prodrug group) which, upon administration to a patient, provides directly or indirectly the present compound or an active metabolite of the present compound. The term "independently" is used herein to indicate that the variable, which is independently applied, varies independently from application to application.

The term "treatment" as used herein includes any treatment of a condition or disease in an animal, particularly a mammal, more particularly a human, and includes: (i) preventing the disease or condition from occurring in a subject which may be predisposed to the disease but has not yet been diagnosed as having it; (ii) inhibiting the disease or condition, i.e. arresting its development; relieving the disease or condition, i.e. causing regression of the condition; or (iii) ameliorating or relieving the conditions caused by the disease, i.e. symptoms of the disease.

The term "subject" refers to mammal including but not limited to rat, monkey and human.

The term "effective" is used to describe an amount of a compound, composition or component which, when used within the context of its intended use, effects an intended result.

The term "therapeutically effective amount" refers to that amount which is sufficient to effect treatment, as defined herein, when administered to a mammal in need of such treatment. The therapeutically effective amount will vary depending on the subject and disease state being treated, the severity of the affliction and the manner of administration, and may be determined routinely by one of ordinary skill in the art.

Suitable routes for administration include oral, peroral, rectal, vassal, topical (including ocular, buccal and sublingual), vaginal and parental (including subcutaneous, intramuscular, intravitreous, intravenous, intradermal, intrathecal and epidural). The preferred route of administration will depend upon the condition of the patient, the toxicity of the compound and the site of infection, among other considerations known to the clinician.

The therapeutic composition of the invention comprises about 1% to about 95% of the active ingredient, single-dose forms of administration preferably comprising about 20% to about 90% of the active ingredient and administration forms which are not single-dose preferably comprising about 5% to about 20% of the active ingredient. Unit dose forms are, for example, coated tablets, tablets, ampoules, vials, suppositories or capsules. Other forms of administration are, for example, ointments, creams, pastes, foams, tinctures, lipsticks, drops, sprays, dispersions and the like. Examples are capsules containing from about 0.05 g to about 1.0 g of the active ingredient.

The pharmaceutical compositions of the present invention are prepared in a manner known per se, for example by means of convention mixing, granulating, coating, dissolving or lyophilizing processes.

Preferably, solutions of the active ingredient, and in addition also suspensions or dispersions, especially isotonic aqueous solutions, dispersions or suspensions, are used, it being possible for these to be prepared before use, for example in the case of lyophilized compositions which comprise the active substance by itself or together with a carrier, for example mannitol. The pharmaceutical compositions can be sterilized and/or comprise excipients, for example preservatives, stabilizers, wetting agents and/or emulsifiers, solubilizing agents, salts for regulating the osmotic pressure and/or buffers, and they are prepared in a manner known per se, for example by means of conventional dissolving or lyophilizing processes. The solutions or suspensions mentioned can comprise viscosity-increasing substances, such as sodium carboxymethylcellulose, carboxymethylcellulose, dextran, polyvinylpyrrolidone or gelatin.

Pharmaceutically acceptable forms include, for example, a gel, lotion, spray, powder, pill, tablet, controlled release tablet, sustained release tablet, rate controlling release tablet, enteric coating, emulsion, liquid, salts, pastes, jellies, aerosols, ointments, capsules, gel caps, or any other suitable form that will be obvious to one of ordinary skill in the art.

Suspensions in oil comprise, as the oily component, the vegetable, synthetic or semi-synthetic oils customary for injection purposes. Oils which may be mentioned are, in particular, liquid fatty acid esters which contain, as the acid component, a long-chain fatty acid having 8-22, in particular 12-22, carbon atoms, for example lauric acid, tridecylic acid, myristic acid, pentadecylic acid, palmitic acid, margaric acid, stearic acid, arachidinic acid, behenic acid or corresponding unsaturated acids, for example oleic acid, elaidic acid, euric acid, brasidic acid or linoleic acid, if appropriate with the addition of antioxidants, for example vitamin E, .beta.-carotene or 3,5-di-tert-butyl-4-hydroxytoluene. The alcohol component of these fatty acid esters has not more than 6 carbon atoms and is mono- or polyhydric, for example mono-, di- or trihydric alcohol, for example methanol, ethanol, propanol, butanol, or pentanol, or isomers thereof, but in particular glycol and glycerol. Fatty acid esters are therefore, for example: ethyl oleate, isopropyl myristate, isopropyl palmitate, "Labrafil M 2375" (polyoxyethylene glycerol trioleate from Gattefosee, Paris), "Labrafil M 1944 CS" (unsaturated polyglycolated glycerides prepared by an alcoholysis of apricot kernel oil and made up of glycerides and polyethylene glycol esters; from Gattefosee, Paris), "Labrasol" (saturated polyglycolated glycerides prepared by an alcoholysis of TCM and made up of glycerides and polyethylene glycol esters; from Gattefosee, Paris) and/or "Miglyol 812" (triglyceride of saturated fatty acids of chain length C8 to C12 from Huls AG, Germany), and in particular vegetable oils, such as cottonseed oil, almond oil, olive oil, castor oil, sesame oil, soybean oil and, in particular, groundnut oil.

The preparation of the injection compositions is carried out in the customary manner under sterile conditions, as are bottling, for example in ampoules or vials, and closing of the containers.

For example, pharmaceutical compositions for oral use can be obtained by combining the active ingredient with one or more solid carriers, if appropriate granulating the resulting mixture, and, if desired, processing the mixture or granules to tablets or coated tablet cores, if appropriate by addition of additional excipients.

Suitable carriers are, in particular, fillers, such as sugars, for example lactose, sucrose, mannitol or sorbitol cellulose preparations and/or calcium phosphates, for example tricalcium phosphate, or calcium hydrogen phosphate, and furthermore binders, such as starches, for example maize, wheat, rice or potato starch, methylcellulose, hydroxypropylmethylcellulose, sodium carboxymethylcellulose and/or polyvinyl-pyrrolidine, and/or, if desired, desintegrators, such as the above mentioned starches, and furthermore carboxymethyl-starch, cross-linked polyvinylpyrrolidone, alginic acid or a salt thereof, such as sodium alginate. Additional excipients are, in particular, flow regulators and lubricants, for example salicylic acid, talc, stearic acid or salts thereof, such as magnesium stearate or calcium stearate, and/or polyethylene glycol, or derivatives thereof.

Coated tablet cores can be provided with suitable coatings which, if appropriate, are resistant to gastric juice, the coatings used being, inter alia, concentrated sugar solutions, which, if appropriate, comprise gum arabic, talc, polyvinylpyrrolidine, polyethylene glycol and/or titanium dioxide, coating solutions in suitable organic solvents or solvent mixtures or, for the preparation of coatings which are resistant to gastric juice, solutions of suitable cellulose preparations, such as acetylcellulose phthalate or hydroxypropylmethylcellulose phthalate.

By "controlled release" it is meant for purposes of the present invention that therapeutically active compound is released from the preparation at a controlled rate or at a specific site, for example, the intestine, or both such that therapeutically beneficial blood levels (but below toxic levels) are maintained over an extended period of time, e.g., providing a 12 hour or a 24 hour dosage form.

The term "rate controlling polymer" as used herein includes hydrophilic polymers, hydrophobic polymers or mixtures of hydrophilic and/or hydrophobic polymers that are capable of retarding the release of the compounds in vivo. In addition, many of the same polymers can be utilized to create an enteric coating of a drug, drug suspension, or drug matrix. It is within the skill of those in the art to modify the coating thickness, permeability, and dissolution characteristics to provide the desired controlled release profile (e.g., drug release rate and locus) without undue experimentation.

Examples of suitable controlled release polymers to be used in this invention include hydroxyalkylcellulose, such as hydroxypropylcellulose and hydroxypropylmethyl-cellulose; poly(ethylene)oxide; alkylcellulose such as ethycellulose and methylcellulose; carboxymethylcellulose; hydrophilic cellulose derivatives; polyethylene glycol; polyvinylpyrrolidone; cellulose acetate; cellulose acetate butyrate; cellulose acetate phthalate; cellulose acetate trimellitate; polyvinylacetate phthalate; hydroxypropylmethylcellulose phthalate; hydroxypropylmethylcellulose acetate succinate; poly(alkyl methacrylate); and poly (vinyl acetate). Other suitable hydrophobic polymers include polymers or copolymers derived from acrylic or methacrylic acid esters, copolymers of acrylic and methacrylic acid esters, zein, waxes, shellac and hydrogenated vegetable oils.

To ensure correct release kinetics, the controlled release preparation of this invention contains about 5 and 75% by weight, preferably about 20 and 50% by weight, more preferably about 30 to 45% by weight controlled release polymer(s) and about 1 to 40% by weight, preferably about 3 to 25% by weight active compounds. The controlled release preparation according to the invention can preferably include auxiliary agents, such as diluents, lubricants and/or melting binders. Preferably, the excipients are selected to minimize the water content of the preparation. Preferably, the preparation includes an antioxidant. Suitable diluents include pharmaceutically acceptable inert fillers such as microcrystalline cellulose, lactose, dibasic calcium phosphate, saccharides, and/or mixtures of any of the foregoing. The diluent is suitably a water soluble diluent. Examples of diluents include microcrystalline cellulose such as Avicel ph112, Avicel pH101 and Avicel pH102; lactose such as lactose monohydrate, lactose anhydrous, and Pharmatose DCL 21; dibasic calcium phosphate such as Emcompress; mannitol; starch; sorbitol; sucrose; and glucose. Diluents are carefully selected to match the specific formulation with attention paid to the compression properties. Suitable lubricants, including agents that act on the flowability of the powder to be compressed are, for example, colloidal silicon dioxide such as Aerosil 200; talc; stearic acid, magnesium stearate, and calcium stearate. Suitable low temperature melting binders include polyethylene glycols such as PEG 6000; cetostearyl alcohol; cetyl alcohol; polyoxyethylene alkyl ethers; polyoxyethylene castor oil derivatives; polyoxyethylene sorbitan fatty acid esters; polyoxyethylene stearates; poloxamers; and waxes.

To improve the stability in the controlled release preparation, an antioxidant compound can be included. Suitable antioxidants include sodium metabisulfite; tocopherols such as alpha, beta, or delta-tocopherol tocopherol esters and alpha-tocopherol acetate; ascorbic acid or a pharmaceutically acceptable salt thereof; ascorbyl palmitate; alkyl gallates such as propyl gallate, Tenox PG, Tenox s-1; sulphites or a pharmaceutically acceptable salt thereof; BHA; BHT; and monothioglycerol.

The controlled release preparation according to the invention preferably can be manufactured by blending the compounds with the controlled release polymer(s) and auxiliary excipients followed by direct compression. Other methods for manufacturing the preparation include melt granulation. Preferred melt granulation techniques include melt granulation together with the rate controlling polymer(s) and diluent(s) followed by compression of the granules and melt granulation with subsequent blending with the rate controlling polymer(s) and diluents followed by compression of the blend. As desired prior to compression, the blend and/or granulate can be screened and/or mixed with auxiliary agents until an easily flowable homogeneous mixture is obtained.

Oral dosage forms of the controlled release preparation according to the invention can be in the form of tablets, coated tablets, enterically coated tablets or can be multiparticulate, such as in the form of pellets or mini-tablets. If desired, capsules such as hard or soft gelatin capsules, can contain the multiparticulates. If desired, the multiparticulate oral dosage forms can comprise a blend of at least two populations of pellets or mini-tablets having different controlled-release in vitro and/or in vivo release profiles. If desired, one of the pellet or mini-tablet populations can comprise immediate release multiparticulate, such as multiparticulates formed by conventional means.

If desired, the controlled release matrix tablets or multiparticulates of this invention can be coated with a controlled release polymer layer so as to provide additional controlled release properties. Suitable polymers that can be used to form this controlled release layer include the rate controlling polymers listed above.

As desired, the tablets, pellets or mini-tablets according to the invention can be provided with a light-protective and/or cosmetic film coating, for example, film-formers, pigments, anti-adhesive agents and plasticizers. Such a film former may consist of fast-dissolving constituents, such as low-viscosity hydroxypropylmethylcelluose, for example Methocel E5 or D14 or Pharmacoat 606 (Shin-Etsu). The film coating may also contain excipients customary in film-coating procedures, such as light-protective pigments, for example iron oxide, or titanium dioxide, anti-adhesive agents, for example talc, and also suitable plasticizers such as PEG 400, PEG 6000, and diethyl phthalate or triethyl citrate.

The controlled release polymer of this invention may consist of a hydrogel matrix. For instance, the compounds can be compressed into a dosage form containing a rate controlling polymer, such as HPMC, or mixture of polymers which when wet will swell to form a hydrogel. The rate of release from this dosage form is controlled both by diffusion from the swollen tablet mass and by erosion of the tablet surface over time. The rate of release may be controlled both by the amount of polymer per tablet and by the inherent viscosities of the polymers used.

Dyes or pigments can be admixed to the tablets or coated tablet coatings, for example for identification or characterization of different doses of active ingredient.

Pharmaceutical compositions, which can be used orally, are also hard capsules of gelatin and soft, closed capsules of gelatin and a plasticizer, such as glycerol or sorbitol. The hard capsules can contain the active ingredient in the form of granules, mixed for example with fillers, such as maize starch, binders and/or lubricants, such as talc or magnesium stearate, and stabilizers if appropriate. In soft capsules, the active ingredient is preferably dissolved or suspended in suitable liquid excipients, such as greasy oils, paraffin oil or liquid polyethylene glycols or fatty acid esters of ethylene glycol or propylene glycol, it being likewise possible to add stabilizers and detergents, for example of the polyethylene sorbitan fatty acid ester type.

Other oral forms of administration are, for example, syrups prepared in the customary manner, which comprise the active ingredient, for example, in suspended form and in a concentration of about 5% to 20%, preferably about 10% or in a similar concentration which results in a suitable individual dose, for example, when 5 or 10 ml are measured out. Other forms are, for example, also pulverulent or liquid concentrates for preparing of shakes, for example in milk. Such concentrates can also be packed in unit dose quantities.

Pharmaceutical compositions, which can be used rectally, are, for example, suppositories that comprise a combination of the active ingredient with a suppository base. Suitable suppository bases are, for example, naturally occurring or synthetic triglycerides, paraffin hydrocarbons, polyethylene glycols or higher alkanols.

Compositions which are suitable for parenteral administration are aqueous solutions of an active ingredient in water-soluble form, for example of water-soluble salt, or aqueous injection suspensions, which comprise viscosity-increasing substances, for example sodium carboxymethylcellulose, sorbitol and/or dextran, and if appropriate stabilizers. The active ingredient can also be present here in the form of a lyophilisate, if appropriate together with excipients, and be dissolved before parenteral administration by addition of suitable solvents. Solutions such as are used, for example, for parental administration can also be used as infusion solutions. Preferred preservatives are, for example. Antioxidants, such as ascorbic acid, or microbicides, such as sorbic or benzoic acid.

Ointments are oil-in-water emulsions, which comprise not more than 70%, but preferably 20-50% of water or aqueous phase. The fatty phase consists, in particular, hydrocarbons, for example vaseline, paraffin oil or hard paraffin's, which preferably comprise suitable hydroxy compounds, such as fatty alcohol's or esters thereof, for example cetyl alcohol or wool wax alcohols, such as wool wax, to improve the water-binding capacity. Emulsifiers are corresponding lipophilic substances, such as sorbitan fatty acid esters (Spans), for example sorbitan oleate and/or sorbitan isostearate. Additives to the aqueous phase are, for example, humectants, such as polyalcohols, for example glycerol, propylene glycol, sorbitol and/or polyethylene glycol, or preservatives and odoriferous substances.

Fatty ointments are anhydrous and comprise, as the base, in particular, hydrocarbons, for example paraffin, vaseline or paraffin oil, and furthermore naturally occurring or semi-synthetic fats, for example hydrogenated coconut-fatty acid triglycerides, or, preferably, hydrogenated oils, for example hydrogenated groundnut or castor oil, and furthermore fatty acid partial esters of glycerol, for example glycerol mono- and/or distearate, and for example, the fatty alcohols. They also contain emulsifiers and/or additives mentioned in connection with the ointments which increase uptake of water.

Creams are oil-in-water emulsions, which comprise more than 50% of water. Oily bases used are, in particular, fatty alcohols, for example lauryl, cetyl or stearyl alcohols, fatty acids, for example palmitic or stearic acid, liquid to solid waxes, for example isopropyl myristate, wool wax or beeswax, and/or hydrocarbons, for example vaseline (petrolatum) or paraffin oil. Emulsifiers are surface-active substances with predominantly hydrophilic properties, such as corresponding nonionic emulsifiers, for example fatty acid esters of polyalcohols or ethyleneoxy adducts thereof, such as polyglyceric acid fatty acid esters or polyethylene sorbitan fatty esters (Tweens), and furthermore polyoxyethylene fatty alcohol ethers or polyoxyethylene fatty acid esters, or corresponding ionic emulsifiers, such as alkali metal salts of fatty alcohol sulfates, for example sodium lauryl sulfate, sodium cetyl sulfate or sodium stearyl sulfate, which are usually used in the presence of fatty alcohols, for example cetyl stearyl alcohol or stearyl alcohol. Additives to the aqueous phase are, inter alia, agents which prevent the creams from drying out, for example polyalcohols, such as glycerol, sorbitol, propylene glycol and/or polyethylene glycols, and furthermore preservatives and odoriferous substances.

Pastes are creams and ointments having secretion-absorbing powder constituents, such as metal oxides, for example titanium oxide or zinc oxide, and furthermore talc and/or aluminum silicates, which have the task of binding the moisture or secretions present.

Foams are administered from pressurized containers and they are liquid oil-in-water emulsions present in aerosol for. As the propellant gases, halogenated hydrocarbons, such as chlorofluoro-lower alkanes, for example dichlorofluoromethane and dichlorotetrafluoroethane, or, preferably, non-halogenated gaseous hydrocarbons, air, $N_2O$, or carbon dioxide are used. The oily phases used are, inter alia, those mentioned above for ointments and creams, and the additives mentioned there are likewise used.

Tinctures and solutions usually comprise an aqueous-ethanolic base to which, humectants for reducing evaporation, such as polyalcohols, for example glycerol, glycols and/or polyethylene glycol, and re-oiling substances, such as fatty acid esters with lower polyethylene glycols, i.e. lipophilic substances soluble in the aqueous mixture to substitute the fatty substances removed from the skin with the ethanol, and, if necessary, other excipients and additives, are admixed.

Methods of Treatment

The invention also relates to a process or method for treatment of the disease states. The chimeric compounds can be administered prophylactically or therapeutically as such or in the form of pharmaceutical compositions, preferably in an amount, which is effective against the diseases mentioned. With a warm-blooded animal, for example a human, requiring such treatment, the compounds are used, in particular, in the form of pharmaceutical composition. A daily dose of about 0.1 to about 5 g, preferably 0.5 g to about 2 g, of a compound of the present invention is administered here for a body weight of about 70 kg.

The description provides methods of treating a disease or disorder or ameliorating the effects of the same comprising the steps of administering to an individual in need thereof, a composition comprising an effective amount of a chimeric compound as described herein, and a pharmaceutically acceptable carrier or excipient, wherein the composition is effective for treating, preventing or ameliorating the effects of the disease or disorder.

The compounds described above are used for the manufacture of a medication for use in the treatment of a disease, disorder or condition. The term "disease involving deregulation of cell proliferation and/or angiogenesis" means, in the context of the invention, any human or animal disease affecting one or more organs. Exemplary diseases include, but are not limited to, rheumatoid arthritis, osteoarthritis, juvenile chronic arthritis, Lyme arthritis, psoriatic arthritis, reactive arthritis, spondyloarthropathy, systemic lupus erythematosus, Crohn's disease, ulcerative colitis, inflammatory bowel disease, insulin dependent diabetes mellitus, thyroiditis, asthma, allergic diseases, psoriasis, dermatitis scleroderma, atopic dermatitis, graft versus host disease, organ transplant rejection, acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlein purpurea, microscopic vasculitis of the kidneys, chronic active hepatitis, uveitis, septic shock, toxic shock syndrome, sepsis syndrome, cachexia, infectious diseases, parasitic diseases, acquired immunodeficiency syndrome, acute transverse myelitis, Huntington's chorea, Parkinson's disease, Alzheimer's disease, stroke, primary biliary cirrhosis, hemolytic anemia, malignancies, heart failure, myocardial infarction, Addison's disease, sporadic, polyglandular deficiency type I and polyglandular deficiency type II, Schmidt's syndrome, adult (acute) respiratory distress syndrome, alopecia, alopecia areata, seronegative arthopathy, arthropathy, Reiter's disease, psoriatic arthropathy, ulcerative colitic arthropathy, enteropathic synovitis, chlamydia, yersinia and salmonella associated arthropathy, spondyloarthopathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis C, common varied immunodeficiency (common variable hypogammaglobulinaemia), dilated cardiomyopathy, female infertility, ovarian failure, premature ovarian failure, fibrotic lung disease, cryptogenic fibrosing alveolitis, post-inflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjogren's disease associated lung disease, ankylosing spondylitis associated lung disease, vasculitic diffuse lung disease, haemosiderosis associated lung disease, drug-induced interstitial lung disease, radiation fibrosis, bronchiolitis obliterans, chronic eosinophilic pneumonia, lymphocytic infiltrative lung disease, post-infectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycemia, type B insulin resistance with acanthosis nigricans, hypoparathyroidism, acute immune disease associated with organ transplantation, chronic immune disease associated with organ transplantation, osteoarthrosis, primary sclerosing cholangitis, idiopathic leucopenia, autoimmune neutropenia, renal disease NOS, glomerulonephritides, microscopic vasulitis of the kidneys, lyme disease, discoid lupus erythematosus, male infertility idiopathic or NOS, sperm autoimmunity, multiple sclerosis (all subtypes), insulin-dependent diabetes mellitus, sympathetic ophthalmia, pulmonary hypertension secondary to connective tissue disease, Goodpasture's syndrome, pulmonary manifestation of polyarteritis nodosa, acute rheumatic fever, rheumatoid spondylitis, Still's disease, systemic sclerosis, Takayasu's disease/arteritis, autoimmune thrombocytopenia, idiopathic thrombocytopenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis and vitiligo. The human antibodies, and antibody portions of the invention can be used to treat autoimmune diseases, in particular those associated with inflammation, including, rheumatoid spondylitis, allergy, autoimmune diabetes, autoimmune uveitis.

The methods herein include administering to the subject (including a subject identified as in need of such treatment) an effective amount of a compound described herein, or a composition described herein to produce a desired effect. Identifying a subject in need of such treatment can be in the judgment of the subject or a health care professional and can be subjective (e.g., opinion) or objective (e.g., measurable by a test or diagnostic method). The therapeutic methods of the invention, which include prophylactic treatment, in general comprise administration of a therapeutically effective amount of at least one of the compounds herein, such as a compound of the formulae herein to a subject (e.g., animal, human) in need thereof, including a mammal, particularly a human. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like).

In another aspect, the present description provides methods of making and using the peptide-oligourea chimeric compounds as described herein. For example, the peptide-oligourea chimeric compounds as described herein can be used as a diagnostic agent or a therapeutic agent for the treatment of a disease or condition.

In one embodiment, the invention provides a method of monitoring treatment progress. The method includes the step of determining a level of diagnostic marker (Marker) (e.g., any target delineated herein modulated by a compound herein, a protein or indicator thereof, etc.) or diagnostic measurement (e.g., screen, assay) in a subject suffering from or susceptible to a disorder or symptoms thereof associated with protein-expression related disease (including misfolding), in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In certain embodiments, a second level of Marker in the subject is determined at a time point later than the determination of the first level, and the two levels are compared to monitor the course of disease or the efficacy of the therapy. In certain embodiments, a pre-treatment level of Marker in the subject is determined prior to beginning treatment according to this invention; this pre-treatment level of Marker can then be compared to the level of Marker in the subject after the treatment commences, to determine the efficacy of the treatment.

The active compound is included in the pharmaceutically acceptable carrier or diluent in an amount sufficient to deliver to a patient a therapeutically effective amount for the desired indication, without causing serious toxic effects in the patient treated. A preferred dose of the active compound for all of the herein-mentioned conditions is in the range from about 10 ng/kg to 300 mg/kg, preferably 0.1 to 100 mg/kg per day, more generally 0.5 to about 25 mg per kilogram body weight of the recipient/patient per day. A typical topical dosage will range from 0.01-5% wt/wt in a suitable carrier. The compound is conveniently administered in any suitable unit dosage form, including but not limited to one containing less than 1mg, 1 mg to 3000 mg, preferably 5 to 500 mg of active ingredient per unit dosage form. An oral dosage of about 25-250 mg is often convenient. The active ingredient is preferably administered to achieve peak plasma concentrations of the active compound of about 0.00001-30 mM, preferably about 0.1-30 µM.

This may be achieved, for example, by the intravenous injection of a solution or formulation of the active ingredient, optionally in saline, or an aqueous medium or administered as a bolus of the active ingredient. Oral administration is also appropriate to generate effective plasma concentrations of active agent. The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

The contents of all references, patents, pending patent applications and published patents, cited throughout this application are hereby expressly incorporated by reference.

Those skilled in the art will recognize, or be able to ascertain using no more than routine experimentation, many equivalents to the specific embodiments of the invention described herein. Such equivalents are intended to be encompassed by the following claims. It is understood that the detailed examples and embodiments described herein are given by way of example for illustrative purposes only, and are in no way considered to be limiting to the invention. Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described. Additional advantageous features and functionalities associated with the systems, methods, and processes of the present invention will be apparent from the appended claims. Moreover, those skilled in the art will recognize, or be able to ascertain using no more than routine experimentation, many equivalents to the specific embodiments of the invention described herein. Such equivalents are intended to be encompassed by the following claims.

The invention claimed is:

1. A catalytic foldamer compound consisting of an oligomer of at least 4 urea-containing residues selected from the formula

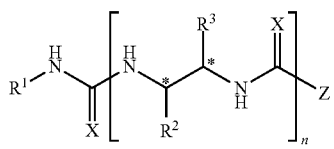

wherein:
n is≥4;
X and each Y is independently selected from O and S;
R¹ is a fluoroalkyl substituted aryl;
each R² is independently selected from the group consisting of hydrogen; side chain of a natural amino acid; fluorine; linear, branched or cyclic C1-C6-alkyl, alkenyl or alkynyl; C1-C6-alkyloxy
each R³ is independently selected from the group consisting of hydrogen; any side chain of a natural amino acid; fluorine; linear, branched or cyclic C1-C6-alkyl, alkenyl or alkynyl; C1-C6-alkyloxy; and
Z is —NH-alkyl or a short oligomer of at least two residues selected from the group consisting of C-substituted and unsubstituted N-2-aminoethylcarbamoyl residue, C-substituted and unsubstituted N-(2-aminoethyl)carbamothioyl residues, C-substituted and unsubstituted N-(2-aminoethyl) urea residues, C-substituted and unsubstituted γ-amino acid residue, —C-substituted and unsubstituted α-amino acids, and any combination thereof.

2. The compound of claim 1, wherein the selected compound includes a total number of from 4 to 15 urea-containing residues.

3. The compound of claim 1, wherein R¹ is 3,5-bis(trifluoromethyl)phenyl.

4. The compound of claim 1, wherein Z is selected from the group consisting of C-substituted and unsubstituted N-(2-aminoethyl) urea residues, —NH-alkyl, and any combination thereof.

5. The compound of claim 1, wherein Z is an alpha-peptide.

6. The compound of claim 1, wherein Z is a gamma-peptide comprising C-substituted and unsubstituted γ-amino acid residues.

7. The compound of claim 1, wherein Z is an N,N'-linked oligourea comprising C-substituted and unsubstituted N-2-aminoethylcarbamoyl residues and N-2-aminoethyl urea residues.

8. The compound of claim 1, wherein the compound has the chemical formula:

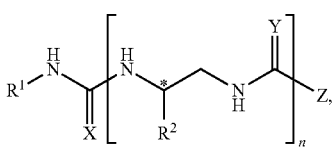

wherein the absolute configuration of C* is the same (either S or R) for the two adjacent residues.

9. The compound of claim 8, wherein the compound has the chemical formula:

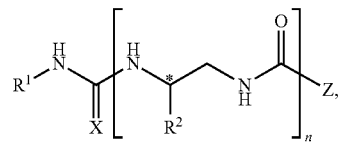

wherein the absolute configuration of C* is the same (either S or R) for the two adjacent residues.

10. The compound of claim 1, wherein the compound has the chemical formula:

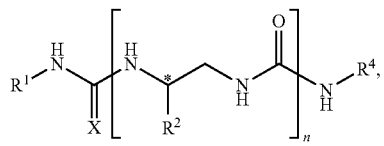

wherein C* is the same (either S or R) for all n residues and R⁴ is an alkyl residue.

11. The compound of claim 1, wherein the compound has the chemical formula:

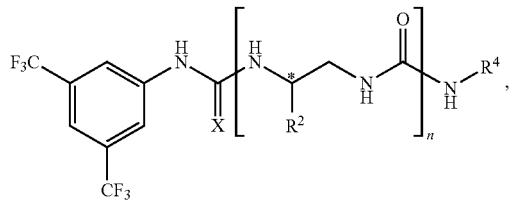

C* is the same (either S or R) for all n residues and R⁴ is an alkyl residue.

12. The compound of claim 1, wherein the compound has the chemical formula:

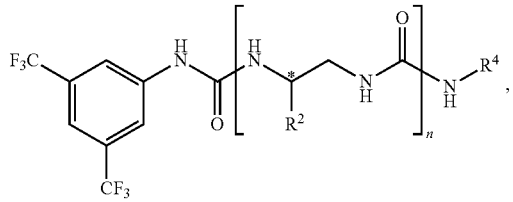

C* is the same (either S or R) for all n residues and R⁴ is an alkyl residue.

13. The compound of claim 1, wherein the Z group is covalently linked to a solid-support, wherein the solid support is further selected from the groups consisting of polystyrene, silica, and polyethylene glycol resins.

14. A catalytic foldamer compound having a structure selected from the structure consisting of:

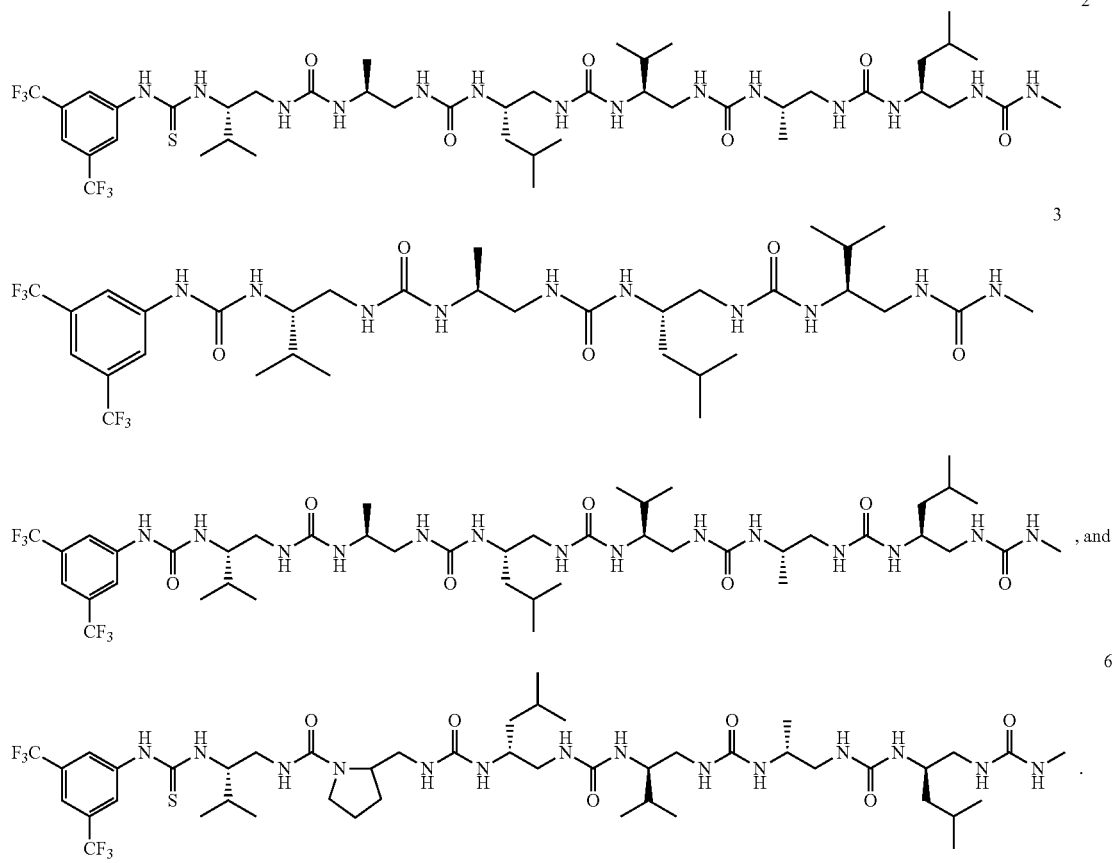

15. The compound of claim 1, wherein the foldamer is a pharmaceutically acceptable acid or base salt.

16. The compound of claim 1, wherein the catalytic foldamer catalyzes at least one reaction selected from the group consisting of: acid catalysis; Michael reaction; 1,2-additions on at least one of C=O, C=N , C=S , C=C, C≡C, C≡N, N=N, N=O, N=S, N≡C, P=O, P=S, and P=N bonds; ring opening of epoxides, aziridines, cyclopropanes, thioepoxides, oxetanes, azetidines, cyclobutanes, or thiooxetanes; addition of nucleophiles; a conjugated addition; a substitution reaction; an elimination reaction; a migration reaction; a Diels alder reactions; electrocyclic reaction; a sigmatropic rearrangement; a dyotropic reaction; a cycloaddition reaction; a reduction reaction; and an oxidation reaction.

17. The compound of claim 1, wherein the catalytic foldamer compound has a structure selected from the structure consisting of:

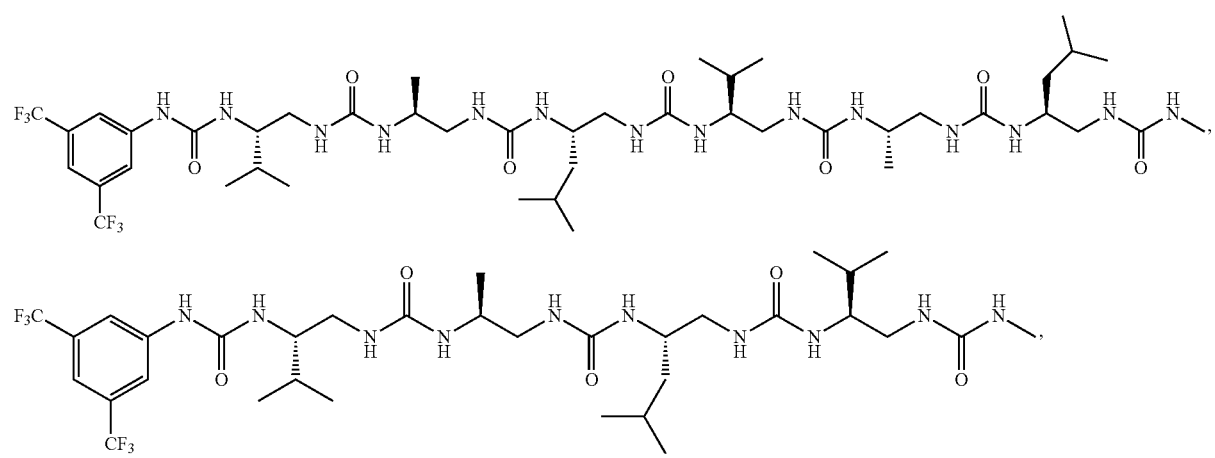

-continued

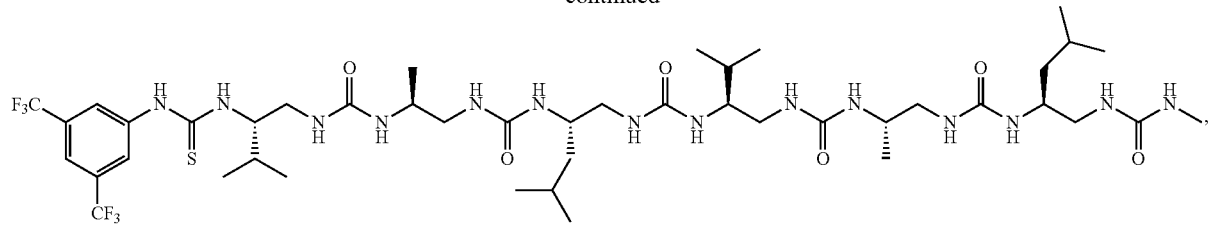

and

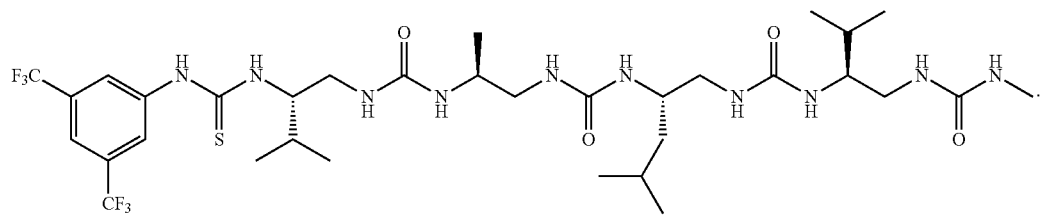

18. The compound of claim 1, wherein Z is a C-substituted and unsubstituted N-(2-aminoethyl) urea residues, C-substituted and unsubstituted γ-amino acid residue, —C-substituted and unsubstituted α-amino acids, —NH-alkyl, and any combination thereof.

19. The compound of claim 3, wherein Z is a C-substituted and unsubstituted N-(2-aminoethyl) urea residues, C-substituted and unsubstituted γ-amino acid residue, —C-substituted and unsubstituted α-amino acids, —NH-alkyl, and any combination thereof.

20. A therapeutic composition comprising an effective amount of a compound of claim 1 or acid or base salt thereof, and a pharmaceutically acceptable excipient.

21. The composition of claim 20, wherein the compound comprises at least one chemical modification selected from the group selected from acetylation, phosphorylation, methylation, glycosylation, prenylation, isoprenylation, farnesylation, geranylation, pegylation, a disulfide bond, and a combination thereof.

* * * * *